(12) United States Patent
Reed et al.

(10) Patent No.: US 8,771,955 B2
(45) Date of Patent: Jul. 8, 2014

(54) DEVICE AND METHOD FOR EXTRACTION AND ANALYSIS OF NUCLEIC ACIDS FROM BIOLOGICAL SAMPLES

(75) Inventors: Michael W. Reed, Lake Forest Park, WA (US); Oliver Z. Nanassy, Edmonds, WA (US)

(73) Assignee: Blood Cell Storage, Inc., Seattle, WA (US)

( * ) Notice: Subject to any disclaimer, the term of this patent is extended or adjusted under 35 U.S.C. 154(b) by 0 days.

(21) Appl. No.: 13/435,440

(22) Filed: Mar. 30, 2012

(65) Prior Publication Data

US 2012/0252017 A1    Oct. 4, 2012

Related U.S. Application Data

(60) Continuation of application No. 12/605,925, filed on Oct. 26, 2009, now Pat. No. 8,148,115, which is a division of application No. 11/768,076, filed on Jun. 25, 2007, now Pat. No. 7,608,399.

(60) Provisional application No. 60/816,577, filed on Jun. 26, 2006, provisional application No. 60/910,609, filed on Apr. 6, 2007.

(51) Int. Cl.
*C12Q 1/68* (2006.01)

(52) U.S. Cl.
CPC .............. *C12Q 1/6851* (2013.01); *C12Q 1/686* (2013.01)
USPC ....................................................... 435/6.12

(58) Field of Classification Search
None
See application file for complete search history.

(56) References Cited

U.S. PATENT DOCUMENTS

| | | |
|---|---|---|
| 4,883,867 A | 11/1989 | Lee et al. |
| 5,155,018 A | 10/1992 | Gillespie et al. |
| 5,234,809 A | 8/1993 | Boom et al. |
| 5,405,519 A | 4/1995 | Schwartz |
| 5,587,128 A | 12/1996 | Wilding et al. |
| 5,599,664 A | 2/1997 | Schwartz |
| 5,658,548 A | 8/1997 | Padhye et al. |
| 5,720,928 A | 2/1998 | Schwartz |
| 5,808,041 A | 9/1998 | Padhye et al. |
| 5,994,056 A | 11/1999 | Higuchi |
| 6,147,198 A | 11/2000 | Schwartz |
| 6,150,089 A | 11/2000 | Schwartz |
| 6,168,948 B1 | 1/2001 | Anderson et al. |
| 6,171,785 B1 | 1/2001 | Higuchi |
| 6,174,671 B1 | 1/2001 | Anantharaman et al. |
| 6,194,562 B1 | 2/2001 | Smith et al. |
| 6,218,531 B1 | 4/2001 | Ekenberg |
| 6,294,136 B1 | 9/2001 | Schwartz |
| 6,340,567 B1 | 1/2002 | Schwartz et al. |
| 6,377,721 B1 | 4/2002 | Walt et al. |
| 6,383,393 B1 | 5/2002 | Colpan et al. |
| 6,448,012 B1 | 9/2002 | Schwartz |
| 6,489,112 B1 | 12/2002 | Hadd et al. |
| 6,509,158 B1 | 1/2003 | Schwartz |
| 6,610,256 B2 | 8/2003 | Schwartz |
| 6,617,105 B1 | 9/2003 | Rudi et al. |
| 6,649,378 B1 | 11/2003 | Kozwich et al. |
| 6,713,263 B2 | 3/2004 | Schwartz |
| 6,720,417 B1 | 4/2004 | Walter |
| 6,814,934 B1 | 11/2004 | Higuchi |
| 6,821,757 B2 | 11/2004 | Sauer et al. |
| 7,173,124 B2 | 2/2007 | Deggerdal et al. |
| 7,238,530 B2 | 7/2007 | Goudsmit et al. |
| 7,385,043 B1 | 6/2008 | Kramer |
| 7,416,892 B2 | 8/2008 | Battrell et al. |
| 2001/0026921 A1 | 10/2001 | Rabbani et al. |
| 2002/0006623 A1 | 1/2002 | Bradley et al. |
| 2002/0025529 A1 | 2/2002 | Quake et al. |
| 2002/0155586 A1 | 10/2002 | Cheng et al. |
| 2002/0157119 A1 | 10/2002 | Beachy et al. |
| 2002/0164816 A1 | 11/2002 | Quake |
| 2003/0138941 A1 | 7/2003 | Gong et al. |
| 2004/0014070 A1 | 1/2004 | Pinsl-Ober et al. |
| 2004/0086930 A1 | 5/2004 | Tereba et al. |
| 2004/0122222 A1 | 6/2004 | Sakurai et al. |
| 2004/0152085 A1 | 8/2004 | Terlesky et al. |
| 2004/0215011 A1 | 10/2004 | Deggerdal et al. |
| 2005/0142565 A1 | 6/2005 | Samper et al. |
| 2005/0191760 A1 | 9/2005 | Heath et al. |
| 2005/0211559 A1 | 9/2005 | Kayyem |
| 2005/0214765 A1 | 9/2005 | Reitan et al. |
| 2006/0029972 A1 | 2/2006 | Lorenz |
| 2006/0166223 A1 | 7/2006 | Reed et al. |
| 2006/0188973 A1 | 8/2006 | Xu et al. |
| 2006/0216239 A1 | 9/2006 | Zhang et al. |
| 2010/0028980 A1 | 2/2010 | Hasson et al. |

FOREIGN PATENT DOCUMENTS

| | | |
|---|---|---|
| EP | 0 430 248 A2 | 6/1991 |
| EP | 1 234 832 B1 | 8/2002 |
| EP | 1 388 588 A1 | 2/2004 |
| EP | 1 529 841 B1 | 5/2005 |

(Continued)

OTHER PUBLICATIONS

Bhattacharyya, A., and C.M. Klapperich, "Thermoplastic Microfluidic Device for On-Chip Purification of Nucleic Acids for Disposable Diagnostics," Analytical Chemistry 78(3):788-792, Feb. 2006.

(Continued)

*Primary Examiner* — James Martinell
(74) *Attorney, Agent, or Firm* — Christensen O'Connor; Johnson Kindness PLLC

(57) ABSTRACT

Device and methods for extracting and analyzing nucleic acids from biological samples.

12 Claims, 24 Drawing Sheets

(56) References Cited

FOREIGN PATENT DOCUMENTS

| | | |
|---|---|---|
| EP | 1 607 748 A1 | 12/2005 |
| WO | 99/09042 A2 | 2/1999 |
| WO | 00/40697 A1 | 7/2000 |
| WO | 02/22265 A1 | 3/2002 |
| WO | 2004/040001 A2 | 5/2004 |
| WO | 2004/061085 A2 | 7/2004 |
| WO | 2004/071662 A1 | 8/2004 |
| WO | 2005/007895 A1 | 1/2005 |
| WO | 2005/066343 A1 | 7/2005 |
| WO | 2005/073691 A1 | 8/2005 |

OTHER PUBLICATIONS

Boom, R., et al., "Rapid and Simple Method for Purification of Nucleic Acids," Journal of Clinical Microbiology 28(3):495-503, Mar. 1990.

Breadmore, M.C., et al., "Microchip-Based Purification of DNA From Biological Samples," Analytical Chemistry 75(8):1880-1886, Apr. 2003.

Cady, N.C., et al., "Nucleic Acid Purification Using Microfabricated Silicon Structures," Biosensors & Bioelectronics 19(1):59-66, Oct. 2003.

"DNA Quantitation Kit, Fluorescence Assay," Product Code: DNA-QF, 2000-2001 Product Catalog: Molecular Biology, Sigma-Aldrich, St. Louis, Mo., at least as early as Jun. 2000, p. 109.

"DNA Quantitation Kit, Fluorescence Assay," Product Information / Technical Bulletin, Catalog No. DNAQF, Sigma-Aldrich, St. Louis, Mo., at least as early as 2001, 4 pages.

Duncan, R.E., and P.T. Gilham, "Isolation of Transfer RNA Isoacceptors by Chromatography on Dihydroxyboryl-Substituted Cellulose, Polyacrylamide, and Glass," Analytical Biochemistry 66(2):532-539, Jun. 1975.

Gao, J., and M.B. Chan-Park, "Adhesive Behavior of DNA Molecules on Silicon Wafers Treated by Argon and Oxygen Plasma," Surface and Coatings Technology 194(2-3):244-250, May 2005.

Gobbers, E., et al., "Efficient Extraction of Virus DNA by NucliSens Extractor Allows Sensitive Detection of Hepatitis B Virus by PCR," Journal of Clinical Microbiology 39(12):4339-4343, Dec. 2001.

Kim, J.-H., et al., "A Disposable DNA Sample Preparation Microfluidic Chip for Nucleic Acid Probe Assay," Proceedings of the 15th IEEE International Conference on Micro Electro Mechanical Systems, Las Vegas, Jan. 20-24, 2002, pp. 133-136.

Lee, C.-Y., Jr., et al., "Integrated Microfluidic Systems for DNA Analysis," Proceedings of the IEEE International Conference on Robotics and Biomimetics, Shenyang, China, Aug. 22-26, 2004, pp. 284-289.

Legendre, L.A., et al., "A Simple, Valveless Microfluidic Sample Preparation Device for Extraction and Amplification of DNA From Nanoliter-Volume Samples," Analytical Chemistry 78(5):1444-1451, Mar. 2006.

Liu, W.-T., and L. Zhu, "Environmental Microbiology-on-a-Chip and Its Future Impacts," Trends in Biotechnology 23(4):174-179, Apr. 2005.

Malic, L., et al., "Current State of Intellectual Property in Microfluidic Nucleic Acid Analysis," Recent Patents on Engineering 1(1):71-88, Feb. 2007.

McCaustland, K.A., et al., "Application of Two RNA Extraction Methods Prior to Amplification of Hepatitis E Virus Nucleic Acid by the Polymerase Chain Reaction," Journal of Virological Methods 35(3):331-342, Dec. 1991.

Münchow, G., et al., "Automated Chip-Based Device for Simple and Fast Nucleic Acid Amplification," Expert Review of Molecular Diagnostics 5(4):613-620, Jul. 2005.

Nakagawa, T., et al., "Fabrication of Amino Silane-Coated Microchip for DNA Extraction From Whole Blood," Journal of Biotechnology 116(2):105-111, Mar. 2005.

Nanassy, O.Z., et al., "Capture of Genomic DNA on Glass Microscope Slides," Analytical Biochemistry 365(2):240-245, Jun. 2007.

Rohland, N., and M. Hofreiter, "Comparison and Optimization of Ancient DNA Extraction," Biotechniques 42(3):343-352, Mar. 2007.

Steiner, J.J., et al., "A Rapid One-Tube Genomic DNA Extraction Process for PCR and RAPD Analyses," Nucleic Acids Research 23(13)2569-2570, Jul. 1995.

Thompson, J.D., et al., "Extraction of Cellular DNA From Crude Cell Lysate With Glass," Nucleic Acids Research 18(4):1074, Feb. 1990.

Tian, H., et al., "Evaluation of Silica Resins for Direct and Efficient Extraction of DNA From Complex Biological Matrices in a Miniaturized Format," Analytical Biochemistry 283(2):175-191, Aug. 2000.

Vogelstein, B., and D. Gillespie, "Preparative and Analytical Purification of DNA From Agarose," PNAS (Proceedings of the National Academy of Sciences USA) 76(2):615-619, Feb. 1979.

Waters, L.C., et al., "Microchip Device for Cell Lysis, Multiplex PCR Amplification, and Electrophoretic Sizing," Analytical Chemistry 70(1):158-162, Jan. 1998.

Weigl, B.H, et al., "Lab-on-a-Chip for Drug Development," Advanced Drug Delivery Reviews 55(3):349-377, Feb. 2003.

Wolfe, K.A., "Toward a Microchip-Based Solid-Phase Extraction Method for Isolation of Nucleic Acids," Electrophoresis 23(5):727-733, Mar. 2002.

Zhong, R., et al., "Fabrication of Two-Weir Structure-Based Packed Columns for On-Chip Solid-Phase Extraction of DNA," Electrophoresis 28(16):2920-2926, Aug. 2007.

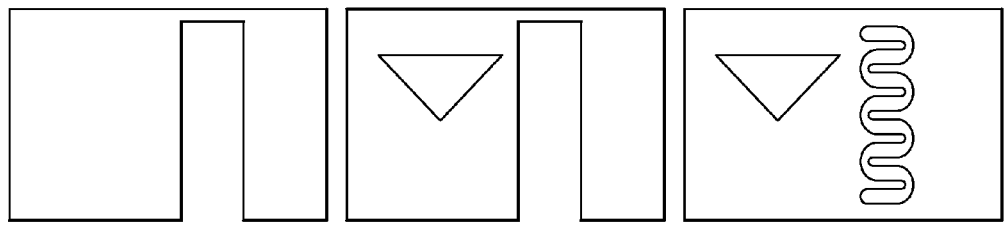
LAYER 1     LAYERS 2 & 3     LAYERS 4 & 5
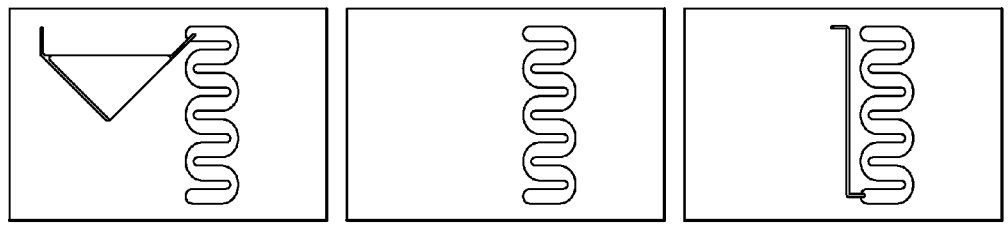
LAYER 6     LAYER 7     LAYER 8
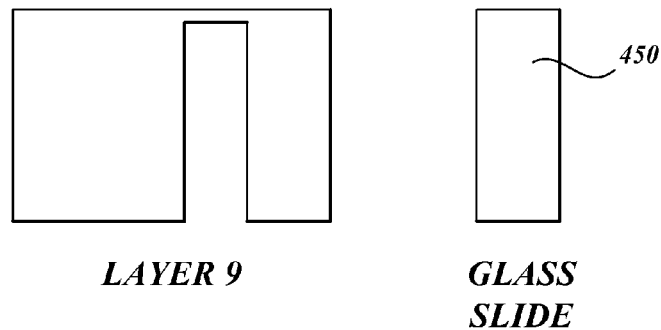
LAYER 9     GLASS SLIDE
*Fig.20A.*

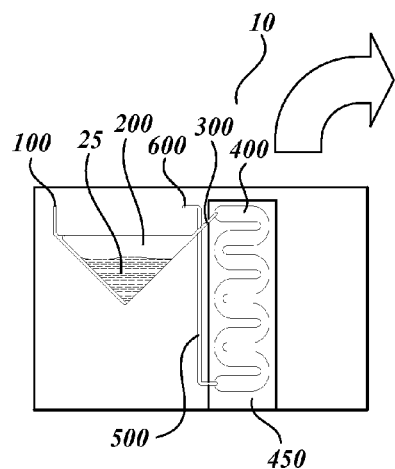
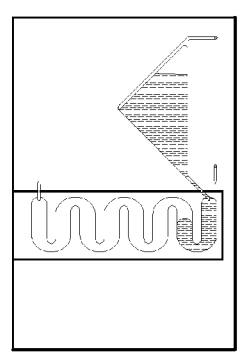
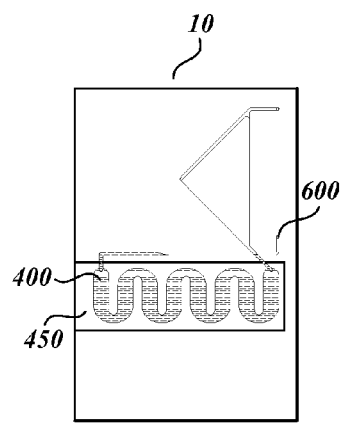
*Fig.21A.*  *Fig.21B.*  *Fig.21C.*
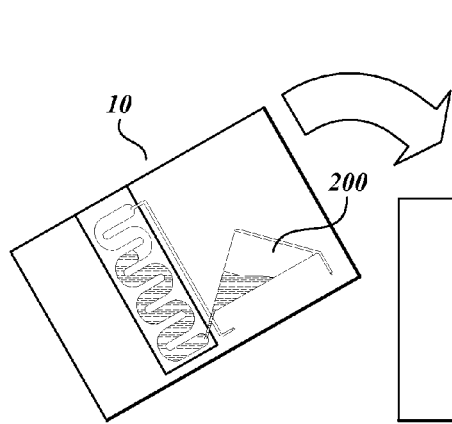
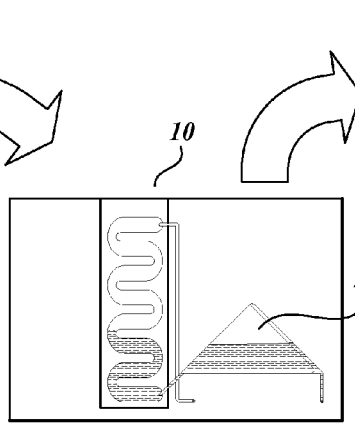
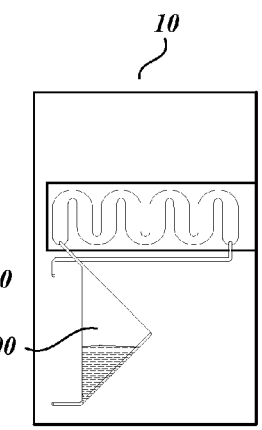
*Fig.21D.*  *Fig.21E.*  *Fig.21F.*

DEVICE AND METHOD FOR EXTRACTION AND ANALYSIS OF NUCLEIC ACIDS FROM BIOLOGICAL SAMPLES

CROSS-REFERENCES TO RELATED APPLICATIONS

This application is a continuation of U.S. patent application Ser. No. 12/605,925, filed Oct. 26, 2009, which is a division of U.S. patent application Ser. No. 11/768,076, filed Jun. 25, 2007, now U.S. Pat. No. 7,608,399, which claims the benefit of U.S. Provisional Application No. 60/816,577, filed Jun. 26, 2006, and U.S. Provisional Application No. 60/910,609, filed Apr. 6, 2007. Each application is expressly incorporated herein by reference in its entirety.

BACKGROUND OF THE INVENTION

Platelets are a component of blood comprised of anucleate megakaryocyte fragments that circulate in the blood for about 10 days. When separated as a component of whole blood, platelets are routinely concentrated, re-suspended in plasma and/or platelet additive solutions, leukoreduced by passage through a filtration device and stored in platelet storage bags which are kept on flatbed agitators for 5 to 7 days at a temperature of 22° C. The relative DNA content in whole blood platelets (WBP) or leukoreduced/apheresis platelets varies considerably.

Microbial contamination of blood transfusion products is a major medical problem. Blood banks are faced with a great challenge in testing each platelet bag for microbial contamination prior to release for infusion into a patient. Currently contaminated platelets are often infused into patients, and the physician is notified subsequently that the platelets were contaminated as the culture results become available. Under the American Association of Blood Banks (A.A.B.B.) standard 5.1.5.1, blood banks or transfusion services are instructed to have methods to limit and detect bacterial contamination in all platelet concentrates. Nucleic Acid Testing (NAT) technology would allow testing of bacterially contaminated units to be detected rapidly after the first day of storage, thus ensuring a safe transfusion by eliminating the possibility of contaminated platelets.

With the successful implementation of stringent control measures, the estimated risk of infection by well known viral pathogens such as HIV and HCV has fallen below 1 per 1 to 2 million transfusion units. This was achieved in part through the use of nucleic acid based testing performed on pooled products composed of 16 to 24 units. In contrast, the risk of transfusion with bacterially contaminated platelets may be as a high as 1 in 1,000 units, with perhaps 10% to 25% of such incidents resulting in adverse effects on patients. A recent study on the microbiological safety of transfusions concluded that a rapid test for microbial contamination in platelets with a detection limit of $10^3$ or $10^4$ organisms/ml is a desirable target.

Vogelstein and Gillespie described the purification of DNA using glass as a DNA binding surface in the presence of high concentrations of chaotropic salts, for example, GuSCN, GuHCl, NaI, or $NaClO_4$. The binding of sequence specific DNA probes to glass microscope slides for use in DNA microarrays was also previously described. The slides were not, however, used for capture of genomic DNA from samples. One advantage of the flat glass microscope slides is the reproducibility of the glass product. Glass microscope slides are made by Erie Scientific (Portsmouth, N.H.) from soda lime glass. Thin glass sheets are drawn from the molten glass using the "electroverre" process and the material is known as "Swiss glass." Glass microscope slides are cut from large thin (1 mm thick) sheets. Glass slides have been used for decades in medical diagnostics and the material is very uniform.

U.S. Pat. No. 5,234,809 describes a one-step process for purification of nucleic acids from complex material such as body fluids or other biological starting materials. In the method, a process is described for isolating nucleic acids from starting material comprising mixing the starting material, a chaotropic substance, and a nucleic acid solid phase such as glass cuvettes, separating the solid phase with the nucleic acid bound to it from the liquid, and washing the solid phase nucleic acid complexes. However, it is well known that such a one-step process often cannot be used to purify a significant amount of the total nucleic acids available in the starting mixture. This can be demonstrated using even known quantities of nucleic acids added to a complex biological fluid—plasma—prior to purification over a well understood commercial DNA purification kit using processes such as those described in U.S. Pat. No. 5,234,809.

For extraction of nucleic acids from blood or blood products, proteolysis of the sample is commonly carried out prior to purification of the DNA. Enzymes such as proteinase K, lysostaphin, or other similar enzymes that are either expressed in organisms such as *Esherichia coli* or *Pichia pastoris* and purified, or purified from other sources, can be used for proteolysis.

NAT is a powerful analytical tool for determining the presence of genetic material (DNA or RNA) in biological samples. For example, polymerase chain reaction (PCR) can be used to detect trace microbial contamination in sterile systems and to find pathogenic gene sequences in the human cells. In blood banks, NAT is commonly used to detect the presence of viral contamination (HIV, HBV, HCV) in blood products.

It has been previously shown using a NAT protocol that the sampling of pooled platelets after one day of storage affords the accurate detection of most bacterial species in spiked platelet concentrates (PCs) at detection levels that equal or exceed the culture systems currently in use for bacterial testing of PCs. The NAT protocol provides an inherent advantage in providing results within a short amount of time in a closed sterile device that would allow for the clinical determination of the level of microbial contamination within a sample.

SUMMARY OF THE INVENTION

The present invention provides a device and method for extracting and analyzing nucleic acids from biological samples. The method and device are useful for determining the quantity of nucleic acids in a sample.

In one aspect, the invention provides a fluorescence method for determining the quantity of nucleic acids in a sample. In one embodiment, the method includes:

(a) introducing a sample containing cells in a liquid medium into a first chamber of a vessel, the vessel comprising the first chamber and a second chamber, wherein the first chamber is in liquid communication with the second chamber and wherein the second chamber has at least a portion of one surface effective for binding nucleic acids;

(b) lysing the cells to provide nucleic acids in the liquid medium;

(c) transferring at least a portion of the liquid medium from the first chamber into the second chamber;

(d) extracting the nucleic acids from the liquid medium by binding the nucleic acids to the surface of the second chamber effective for binding nucleic acids to provide isolated nucleic acids;

(e) contacting the isolated nucleic acids with a fluorescent compound having a fluorescence intensity dependent on the concentration of nucleic acids; and (f) measuring the fluorescence of the fluorescent compound to determine the quantity of isolated nucleic acids.

In one embodiment, the sample is blood or a blood product.

In another aspect of the invention, a method for amplifying and quantifying the amount of nucleic acids in a sample is provided. In one embodiment, the method includes:

(a) introducing a sample containing cells in a liquid medium into a first chamber of a vessel, the vessel comprising the first chamber and a second chamber, wherein the first chamber is in liquid communication with the second chamber and wherein the second chamber has at least a portion of one surface effective for binding nucleic acids;

(b) lysing the cells to provide nucleic acids in the liquid medium;

(c) transferring at least a portion of the liquid medium from the first chamber into the second chamber;

(d) extracting the nucleic acids from the liquid medium by binding the nucleic acids to a surface of the second chamber effective for binding nucleic acids, to provide isolated nucleic acids;

(e) releasing the isolated nucleic acids from the surface of the second chamber effective for binding nucleic acids by contacting the isolated nucleic acids with a buffer solution;

(f) treating the isolated nucleic acids with and a nucleic acid amplification reaction mixture under conditions for amplifying the isolated nucleic acids to provide amplified nucleic acids;

(g) contacting the amplified nucleic acids with a fluorescent compound having a fluorescence intensity dependent on the concentration of nucleic acids; and (h) measuring the fluorescence of the fluorescent compound to determine the quantity of amplified nucleic acids.

In one embodiment the method includes repeating steps (f) and (h) a pre-determined number of times to determine the amount of amplified nucleic acids.

In one embodiment, the method includes contacting the isolated nucleic acids with a fluorescent compound having a fluorescence intensity dependent on the concentration of nucleic acids and measuring the fluorescence of the fluorescent compound to determine the quantity of isolated nucleic acids prior to step (f).

In another aspect of the invention, a fluidic system including a vessel is provided.

The vessel includes:

(a) a fluid inlet port;

(b) a first chamber in fluid communication with the inlet port;

(c) a second chamber in fluid communication with the first chamber, wherein the second chamber has at least one glass surface;

(d) a first channel that connects the first chamber and the second chamber;

(e) a fluid outlet port; and (f) a second channel that connects the second chamber to the fluid outlet port.

In one embodiment the fluidic system includes a device for measuring the fluorescent intensity of a fluorescent compound.

In another aspect, the invention provides a method for determining the microbial content of a blood product including:

(a) introducing a sample of a blood product containing cells in a liquid medium into a first chamber of a vessel, the vessel comprising the first chamber and a second chamber, wherein the first chamber is in liquid communication with the second chamber, and wherein the second chamber has at least a portion of one surface effective for binding nucleic acids;

(b) contacting the cells in the liquid medium with a lysis buffer to provide nucleic acids in the liquid medium;

(c) transporting at least a portion of the liquid medium into the second chamber;

(d) extracting the nucleic acids from the liquid medium by binding the nucleic acids to the surface of the second chamber effective for binding nucleic acids to provide isolated nucleic acids;

(e) releasing the isolated nucleic acids from the surface of the second chamber effective for binding nucleic acids by contacting the isolated nucleic acids with an elution buffer to provide released nucleic acids;

(f) contacting the released nucleic acids with a fluorescent compound having a fluorescence intensity dependent on the concentration of nucleic acids and a nucleic acid amplification reaction mixture;

(g) measuring the fluorescence of the fluorescent compound to determine the quantity of released nucleic acids;

(h) treating the released nucleic acids and the nucleic acid amplification reaction mixture under conditions for amplifying the isolated nucleic acids by polymerase chain reaction to provide amplified nucleic acids; and (i) measuring the fluorescence of the fluorescent compound to determine the quantity of amplified nucleic acids.

In one embodiment the method includes repeating steps (h) and (i) a pre-determined number of times to determine the amount of amplified nucleic acids.

In another aspect the invention provides a method for quantifying and amplifying the amount of nucleic acids in a sample. The method includes:

(a) contacting nucleic acids from a sample with a nucleic acid amplification reaction mixture that comprises a first fluorescent compound having a first fluorescence emission maximum and a second fluorescent compound having a second fluorescence emission maximum, wherein the first and second fluorescence emission maxima are different, each having a fluorescence intensity dependent on the concentration of nucleic acids;

(b) measuring the fluorescence of the first fluorescent compound to determine the amount of nucleic acids;

(c) treating the nucleic acids and the nucleic acid amplification reaction mixture under conditions for amplifying the nucleic acids to provide amplified nucleic acids; and (d) measuring the fluorescence of the second fluorescent compound to determine the amount of amplified nucleic acids.

In one embodiment, the nucleic acid amplification reaction mixture further comprises a third fluorescent compound having a third fluorescence emission maximum and a fluorescence intensity dependent on the concentration of amplified nucleic acids, wherein the third fluorescence emission maximum is different from the first and second fluorescence emission maxima.

In another aspect, the invention provides a composition including a nucleic acid amplification reaction mixture and a fluorescent compound. The fluorescent compound has a fluorescence intensity dependent on the concentration of nucleic acids and has a fluorescent emission maximum less than about 500 nm.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 20A is an exploded view of the layers of a representative fluidic device of the invention;

FIGS. 21A-21F are schematic illustrations depicting the transport of fluids through a representative fluidic device of the invention.

DETAILED DESCRIPTION OF THE INVENTION

The present invention provides a device and method for extracting and analyzing nucleic acids from biological samples. The device and method are useful for determining the quantity of nucleic acids in a biological sample. The quantity of nucleic acids is determined by contacting the nucleic acids with a fluorescent compound having a fluorescence intensity dependent on the concentration of nucleic acids and measuring the fluorescence of the fluorescent compound. The device and method of the invention are useful for measuring the quantity of nucleic acids in a blood sample or blood product (e.g., platelets) and determining whether the sample is contaminated with bacterial pathogens.

In one aspect, the invention provides a fluorescence method for determining the quantity of nucleic acids in a sample. In one embodiment, the method includes:

(a) introducing a sample containing cells in a liquid medium into a first chamber of a vessel, the vessel comprising the first chamber and a second chamber, wherein the first chamber is in liquid communication with the second chamber and wherein the second chamber has at least a portion of one surface effective for binding nucleic acids;

(b) lysing the cells to provide nucleic acids in the liquid medium;

(c) transferring at least a portion of the liquid medium from the first chamber into the second chamber;

(d) extracting the nucleic acids from the liquid medium by binding the nucleic acids to the surface of the second chamber effective for binding nucleic acids to provide isolated nucleic acids;

(e) contacting the isolated nucleic acids with a fluorescent compound having a fluorescence intensity dependent on the concentration of nucleic acids; and (f) measuring the fluorescence of the fluorescent compound to determine the quantity of isolated nucleic acids.

Nucleic acids including deoxyribonucleic acids (DNA) or ribonucleic acids (RNA) can be extracted and analyzed by the method. In one embodiment, the sample is blood or a blood product (e.g., platelets) and the nucleic acids that are extracted and analyzed are those from contaminant bacterial pathogens in the blood or blood product.

Figure 1:
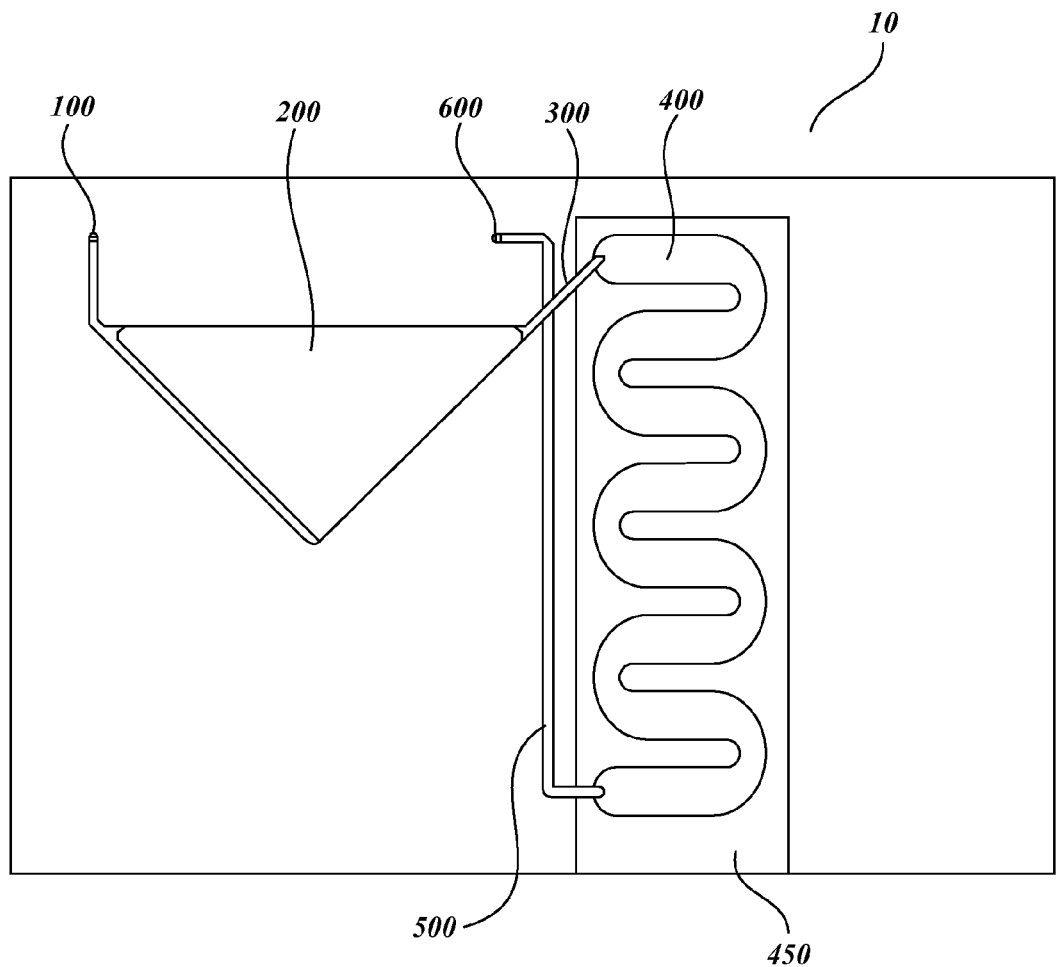
FIG. 1 is a schematic illustration of a representative fluidic device of the invention.

The vessel includes an inlet to the first chamber (lysis chamber), a first channel that connects the first chamber to the second chamber (extraction chamber), an outlet, and a second channel that connects the second chamber to the outlet. A representative vessel useful for carrying out the method of the invention is shown in FIG. 1. Referring to FIG. 1, the representative vessel 10 includes inlet 100, first chamber 200, first channel 300, second chamber 400, second channel 500, and outlet 600. Glass cover 450 defines at least one surface of second chamber 400. In certain embodiments, second chamber 400 is defined by two glass slides (i.e., floor and ceiling of the chamber, see FIG. 20B). The vessel is described below. As used herein, the terms "card" and "DNA card" refer to the vessel of the invention.

In one embodiment, the vessel is sealable. Sealing the vessel reduces the likelihood of environmental contamination of the sample, and reduces the likelihood that a sample handler will be exposed to a contaminated sample.

One feature of the device of the invention is that cells from the sample are lysed in the same vessel in which nucleic acid extraction and analysis is performed. In one embodiment, lysing the cells of the sample comprises contacting the cells with a chaotropic salt solution. Lysing the cells can further include sonicating or mechanically disrupting the cells in the sample in the first chamber.

In the methods, transferring the liquid medium from the first chamber into the second chamber may include rotating the vessel so that the liquid medium is transferred into the second chamber by gravity. Transferring the liquid medium from the first chamber into the second chamber may also include pumping the liquid medium from the first chamber into the second chamber.

Nucleic acids are extracted from the liquid medium in the second chamber by binding to a surface effective to bind nucleic acids to provide isolated nucleic acids. The second chamber includes at least one surface having at least one portion that is effective for binding nucleic acids. In one embodiment, the surface that is effective for binding nucleic acids is a glass surface (flat glass surface). See, for example, surface 450 in FIG. 1. In another embodiment, the surface that is effective for binding nucleic acids is a surface bearing an immobilized agent that is effective for binding nucleic acids (e.g., immobilized minor groove binder or intercalator).

To determine the quantity of isolated nucleic acids, the nucleic acids are contacted with a fluorescent compound having a fluorescent intensity dependent on the concentration of nucleic acids and measuring the fluorescence of the fluorescent compound. Fluorescent compounds having a fluorescent intensity dependent on the concentration of nucleic acids are fluorescent compounds that exhibit a change in fluorescence intensity in the presence of nucleic acids. Useful fluorescent compounds include those compounds whose intensity increases in the presence of nucleic acids. Other useful fluorescent compounds include oligonucleotide probes labeled with both a fluorophore and a quencher and that cleave during nucleic acid amplification releasing fluorophore indicating the presence of specific nucleic acids. Representative fluorescent compounds include fluorogenic minor groove binder agents such as bis-benzimide compounds and intercalating fluorogenic agents such as ethidium bromide. In one embodiment, the fluorescent compound is immobilized in the second chamber. Methods for immobilizing the fluorescent compound in the second chamber and useful fluorescent compounds are described below and in U.S. 2006/0166223 A1, incorporated herein by reference in its entirety. In another embodiment, the method includes releasing the isolated nucleic acids from the surface of the second chamber effective for binding nucleic acids by contacting the isolated nucleic acids with a buffer solution before measuring the fluorescence of the fluorescent compound. In this method, the buffer solution may include the fluorescent compound.

The vessel of the invention allows for the interrogation of the second chamber by fluorescence by having at least a portion of the chamber suitable for transmitting excitation energy to the fluorescent compounds in the second chamber and for transmitting fluorescence emission intensity from the compounds in the second chamber.

In one embodiment, the method further includes purifying the isolated nucleic acids by contacting the isolated nucleic acids with a chaotropic salt solution.

For use in analyzing nucleic acids present in platelets stored in a platelet storage bag, the vessel can be attached directly to the storage bag without contaminating the contents of the bag. In practice, the vessel can be directly attached bag's sampling pouch followed by sterilization of the bag with ethylene oxide using standard conditions. The bag's tubing configuration allows platelet-rich plasma (PRP) to be directly inputted to the vessel with no requirement for aseptic sample handling. For identification control, the bag and card can have the same bar code (or other identifier) for tracking purposes. For example, a PRP sample (about 5 ml) can be drained into a sample bag that is sealed/removed from the storage bag. The removed sample would then be tested by hematology and viral NAT as usual, optionally cultured to enhance possible bacterial contamination, and then a PRP sample (about 0.2 ml) is transferred from the sample bag to the vessel for analysis.

In certain embodiments, the devices and methods of the invention use a glass surface (e.g., a flat glass surface such as a glass slide, see FIG. 1, reference numeral 450) to extract and isolate nucleic acids from a liquid medium. The devices and methods of the invention that use the glass surface nucleic acid capture are referred to herein as the "glass slide" system or method.

Recovery of purified DNA using the glass slide system used in the method and device of the invention was compared to the standard method developed by Qiagen. Recovery of high molecular weight DNA from calf thymus was compared with DNA for bacteriophage lambda using either the glass slide method or the Qiagen Blood Mini Kit. For the Qiagen method, purified DNA was suspended in Tris-EDTA (TE) buffer followed by addition of Qiagen AL Buffer (lysis buffer) and pure ethanol as directed in the package insert, except that protease was not included. Samples were applied to the sample purification columns, washed with wash buffers 1 and 2, and finally eluted with 100 ul TE buffer. For the glass slide protocol, samples were prepared as for the Qiagen method except that 300 ul of the sample was layered onto a glass microscope slide. After 20 minutes of incubation, the slide was washed with Qiagen wash buffers 1 and 2. DNA was eluted from the glass slide with 200 ul of TE buffer. All samples were quantified using the PicoGreen assay (Invitrogen). The results of this experiment were as follows. Using the Qiagen method, recovery of lambda DNA was 94%, and recovery of calf thymus DNA was 20%. Using the glass slide method, recovery of lambda DNA was 20%, and recovery of calf thymus DNA was 20%. The results indicate that even though the recovery of lambda DNA is higher in the Qiagen method, recovery of high molecular weight calf thymus DNA is equivalent between the two systems.

The relatively poor yield of high molecular weight calf thymus DNA from both systems suggests that some property of either the sample preparation protocol or of the sample itself affects the recovery of DNA. One possibility is the size of the DNA substrate used in the binding protocol. To explore this possibility, salmon sperm DNA was purchased from Sigma, suspended in TE buffer, and sonicated for various lengths of time to fractionate or break down the size of the DNA. The size of individual fractions was assessed using agarose gel electrophoresis. Sizes of fractions chosen for binding included (1) unsonicated DNA (>50 Kb); (2) fraction 3 with an average size of >8 Kb; (3) fraction 4 with an average size of 2 to 8 Kb; and (4) fraction 5 (35% power) with an average size of less than 8 Kb with a lower range below that of fraction 4. The results of an experiment showing the effect of sonication on the recovery of DNA using the Qiagen method and glass slide method is shown in FIG. 2.

Figure 2:
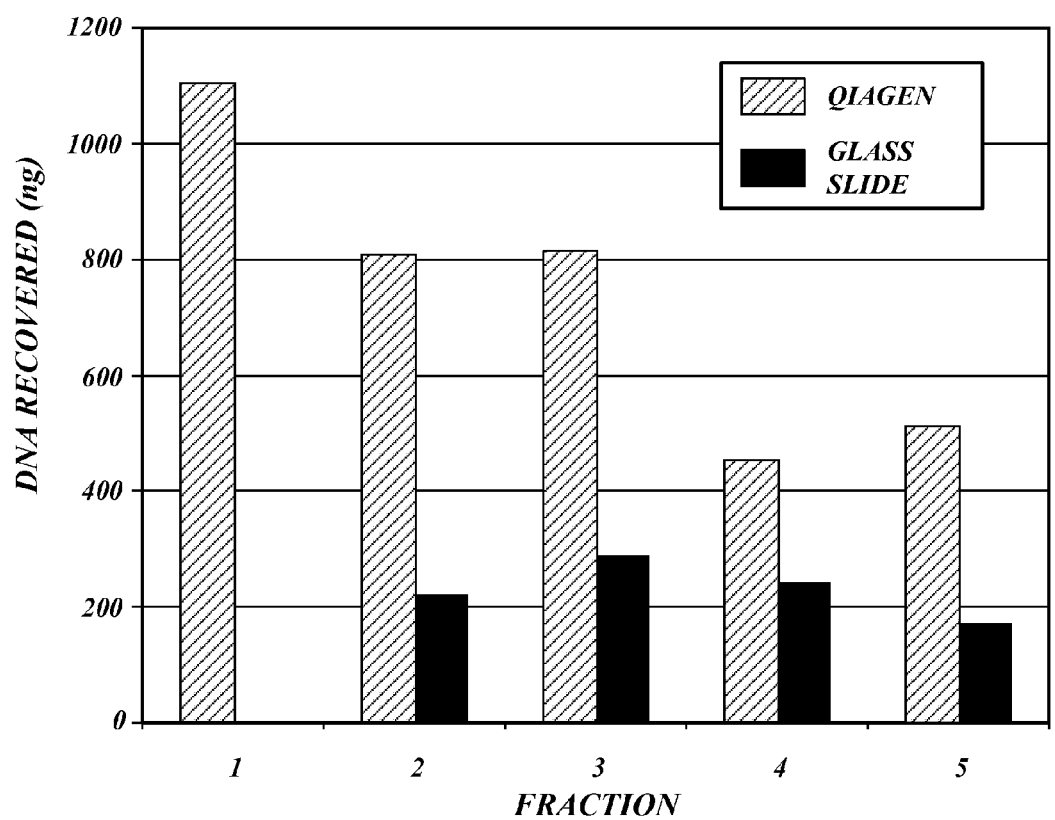
FIG. 2 is a graph comparing the amount of DNA recovered from variously sized DNA fractions by two different methods.

Referring to FIG. 2, fraction 1 corresponds to purified lambda DNA (2.5 ug input). Fraction 2 is unsonicated DNA, fraction 3 is the >8 Kb sonicated fraction, fraction 4 is the 2 to 8 Kb sonicated fraction, and fraction 5 is less than the sonicated >8 Kb fraction. The results show that the recovery of DNA from glass slides is overall less than that of the Qiagen method. In general, with the purified DNA, recovery of DNA is relatively insensitive to the size of the DNA offered to either glass slides or to the Qiagen system. In particular, comparison of unsonicated DNA with fraction 3 DNA (>8 Kb) shows little dependence of size on recovery. This implies that there is little difference in recovery between unsonicated DNA and an 8 Kb size sonicated DNA fraction. A slight effect is seen in the lower sized DNA.

Reagents were developed and compared to the commercially available Qiagen reagents. A set of recipes was used that included a lysis/extraction buffer containing 5M guanidine thiocyanate, 20 mM EDTA, and 1% Triton in 0.1M Tris pH 6.4. Wash buffer 1 had the same composition except that it lacked the Triton. Wash buffer 2 had 10 mM Tris pH 7.4, 2.5 mM EDTA, 50 mM NaCl, and 50% ethanol. The elution buffer contained 10 mM Tris pH 8.0 and 1 mM EDTA (TE buffer).

Figure 3:
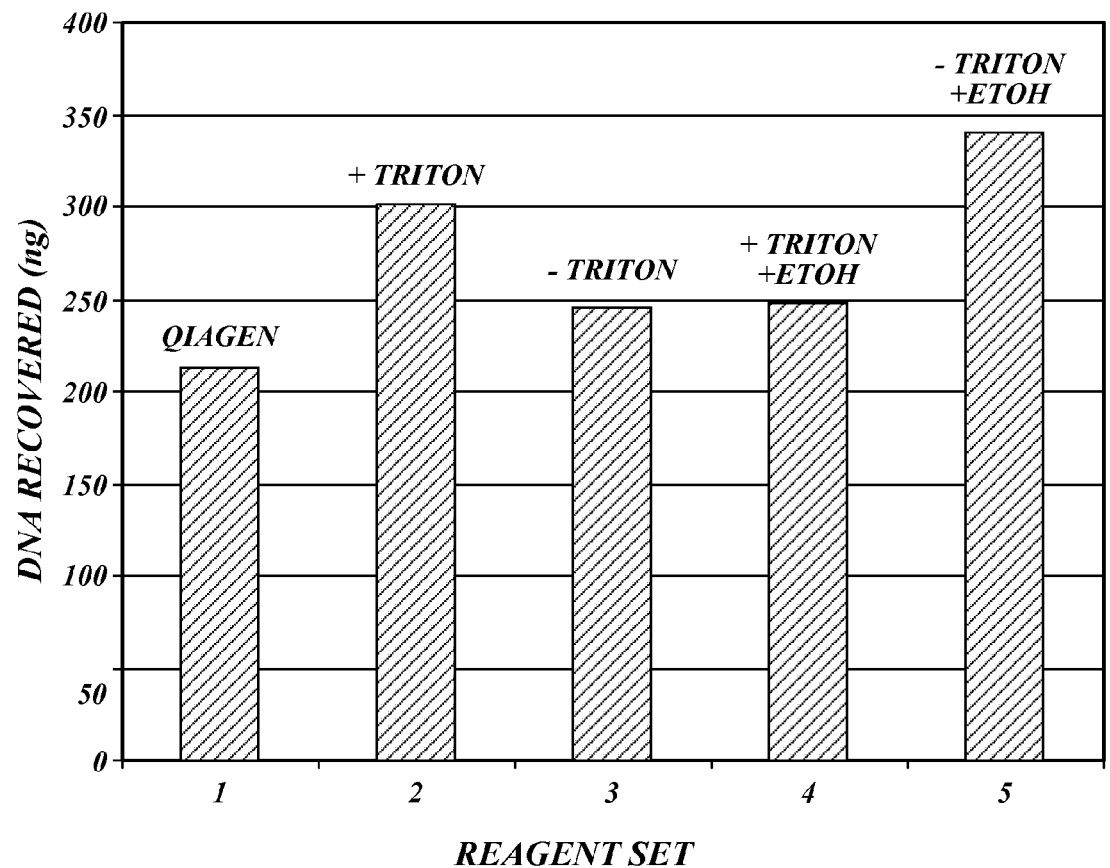
FIG. 3 is a graph comparing the amount of DNA recovered by a representative method of the invention using different reagent formulations.

In contrast to the Qiagen formulations for AL Buffer (lysis buffer) which uses an addition of ethanol, no ethanol dilution is required for the reagents useful in the methods of the invention. The lysis/extraction buffer may be used with no further additions. If a protease is required for lysis, the lysis/extraction buffer is diluted. To assess the effectiveness of the reagent formulations, a slide binding assay was run using 2.5 ug of sonicated DNA (>8 Kb size fraction) to compare DNA yield using the new reagents to DNA yield using the Qiagen reagents. The results are shown in FIG. 3. In this experiment, various combinations of reagents were tested. Referring to FIG. 3, the full reagent set is represented by the designation "+Triton". Triton was left out ("−Triton"), ethanol was added along with triton to mimic the Qiagen reagent set ("+Triton +EtOH"), and again triton was excluded ("−Triton +EtOH"). Although some minor differences were obtained in this experiment, none of the reagent sets varied significantly from the Qiagen reagent set. This indicated that the defined reagent set can effectively substitute for the Qiagen reagent set in the DNA binding assay.

Figure 4:
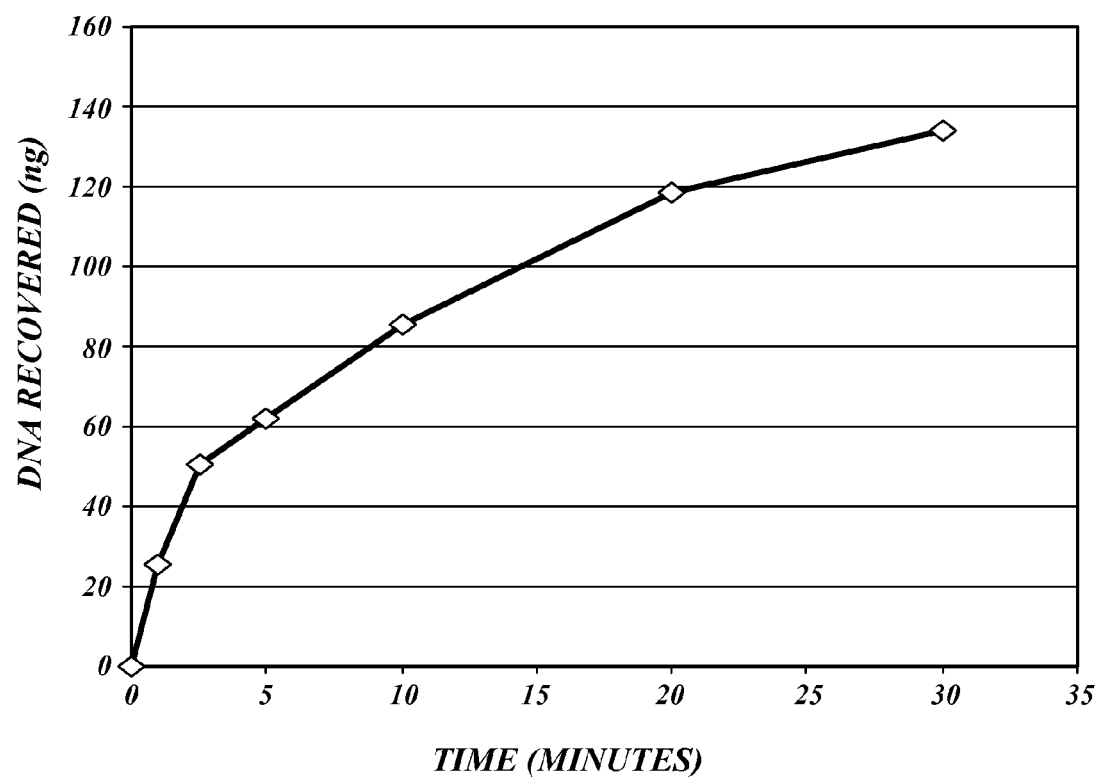
FIG. 4 is a graph showing the amount of DNA recovered as a function of binding time using a representative method of the invention.

To determine the optimum binding and release times for glass slides, the time needed for DNA adsorption was measured. First, 500 ng of unsonicated DNA was suspended in 300 ul of lysis/extraction buffer and applied to a glass slide for time periods ranging from 0 to 35 minutes. Binding was halted by centrifugation of the DNA binding mix from the glass slide. The glass slides were rinsed in wash buffers 1 and 2. DNA was eluted from the glass slides using 200 ul of TE buffer. The results are shown in FIG. 4. Referring to FIG. 4, binding increases over the entire time period of the experiment from 5 minute to 30 minutes. Binding is starting to level off at 30 minutes although a slight increase is still seen at this point. However, over 85% of binding has occurred in the first 20 minutes of the binding curve. Previous data was collected with a 10 minute binding time. The percent recovery increases over this 10 minute time period from about 16% to over 24%. Therefore, a time period for binding of at least 20 minutes is preferred.

Figure 5:
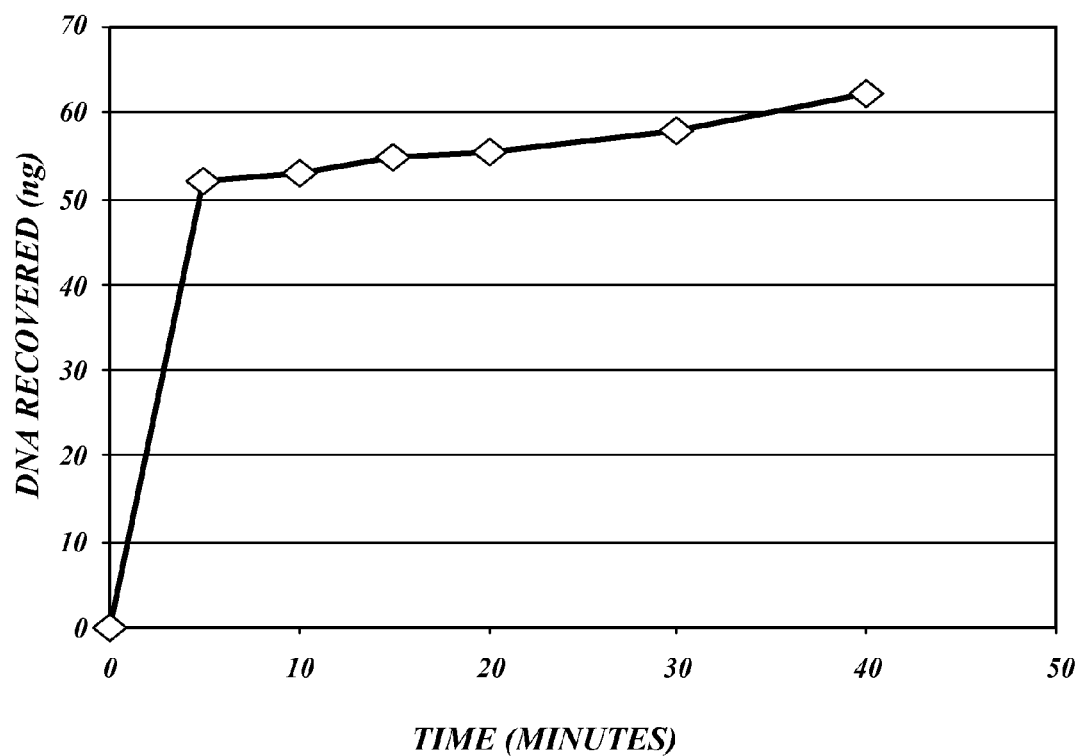
FIG. 5 is a graph showing the amount of DNA recovered as a function of elution time using a representative method of the invention.

The kinetics of elution of high molecular weight DNA was similarly followed. A set of slides was prepared in which unsonicated salmon sperm DNA was bound. The elution step was initiated by layering on TE buffer for the indicated periods of time. The time course was stopped by centrifugation of individual slides. The results are presented in FIG. 5. Referring to FIG. 5, the results show that the most of the DNA has been eluted at only 5 minutes into the time course.

Figure 6:
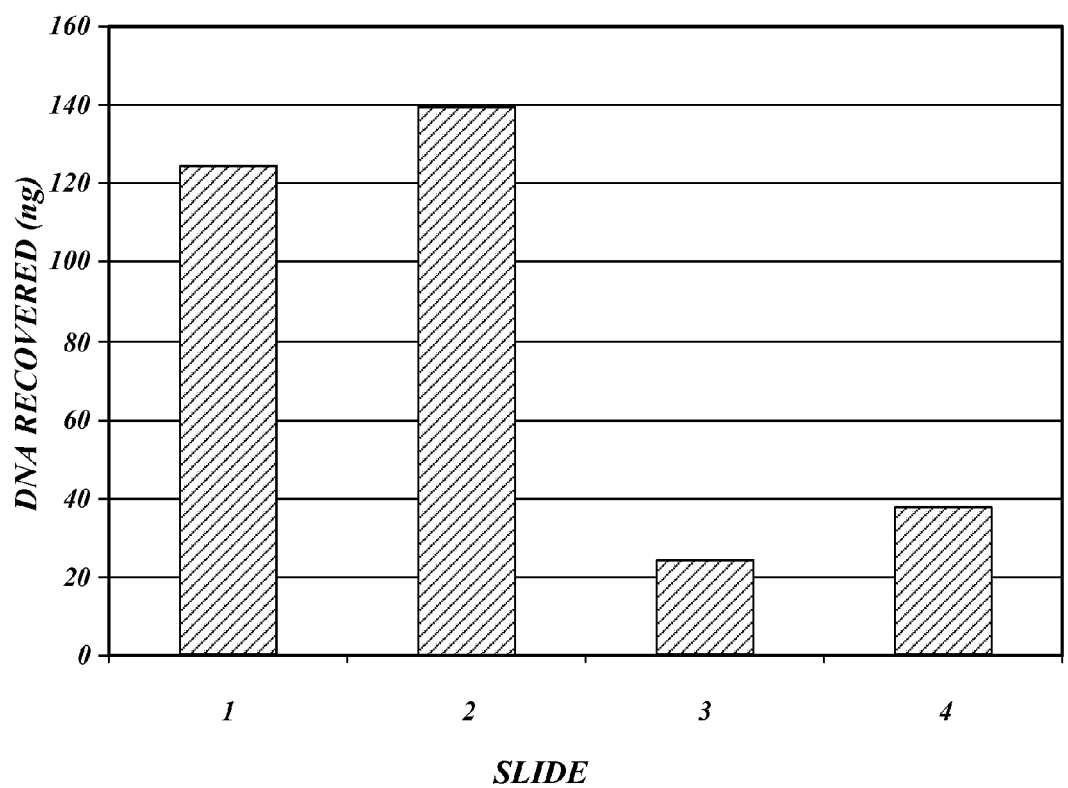
FIG. 6 is a graph comparing the amount of DNA recovered from slides subjected to different temperatures during binding and elution.

Another factor that may influence the slide binding assay is the application of heat either to the binding phase, or elution, or both. Referring to FIG. 6, the effect of temperature was tested in a standard slide binding assay in which 500 ng of unsonicated DNA was suspended in 300 ul of lysis/extraction buffer and applied to slides. Two slides were incubated at 56° C. for 15 minutes (to minimize evaporation) while two slides were incubated at room temperature. Slides were then rinsed in wash buffers 1 and 2. DNA was eluted in 200 ul TE buffer either at 56° C. or at room temperature. Referring again to FIG. 6, Slide 1 had room temperature binding and elution. Slide 2 had room temperature binding and 56° C. elution. Slide 3 had 56° C. binding and room temperature elution. Slide 4 had 56° C. binding and 56° C. elution. The results in FIG. 6 show that a reproducible effect of elution at 56° C. is observed that ranges from 5% to 20% increase in DNA recovered. Heating at the binding stage of the protocol greatly decreases the amount of DNA that one can expect to recover from glass slides.

Figure 7:
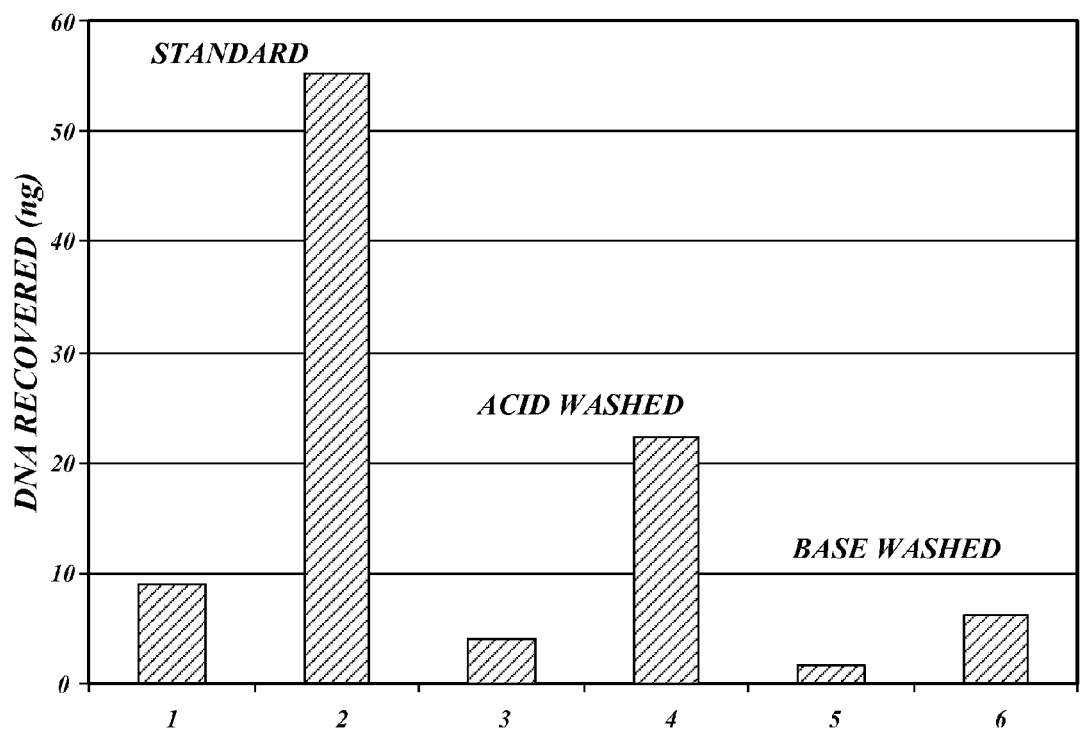
FIG. 7 is a graph comparing the amount of DNA recovered from slides that were pre-treated using various cleaning protocols.

The need for extra cleaning of slides and slide-to-slide reproducibility was also studied to determine whether the cleanliness of the glass slides has an influence on binding and recovery of DNA. The yield of recovered DNA was thought to be increased if the glass slides were cleaned thoroughly with acid or base. Referring to FIG. 7, glass slides were washed in either 1N nitric acid or sodium hydroxide and then tested in the slide binding assay. This experiment was done with DNA at both 100 and 500 ng total input. Both the acid and base washed slides were found to have a greatly decreased amount of DNA recovered as opposed to the standard slides that were not further cleaned. The results shown in FIG. 7 suggest that further cleaning of glass slides is detrimental to efficient slide binding.

Figure 8:
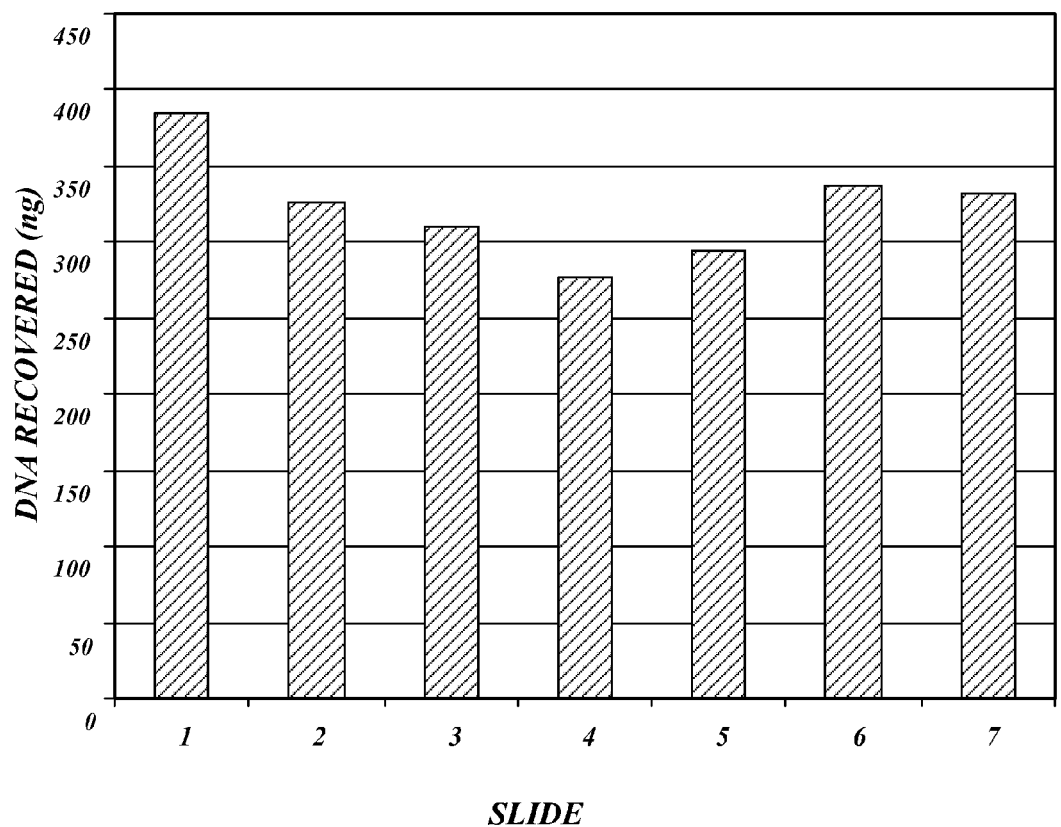
FIG. 8 is a graph comparing the amount of DNA recovered from different slides under similar conditions.

An assay was also performed in which the slide-to-slide variation was measured. Referring to FIG. 8, a series of slides were prepared in which 500 ng of total input unsonicated DNA was bound to each slide with a binding time of 30 minutes. Slides were rinsed in wash buffer 1 and 2, and DNA was eluted with 200 ul TE buffer. A total of 16 slides were tested. One representative set is shown in FIG. 8. The standard glass slide surface gave consistent DNA recovery. Out of 16 slides, one slide was very low and was discarded from the analysis. Of the remaining slides, the standard deviation was 10%. The average yield on the slides in FIG. 8 is about 300 ng of DNA, meaning that the average percent yield is approximately 60%.

DNA recovery on glass slides is reduced, but not destroyed, when the DNA is suspended in biological media. In the presence of a physiological amount of human serum albumin (HSA), the DNA recovery is reduced 32%. When 25% plasma is added to the DNA/lysis buffer mix, recovery is reduced 75%.

Figure 9:
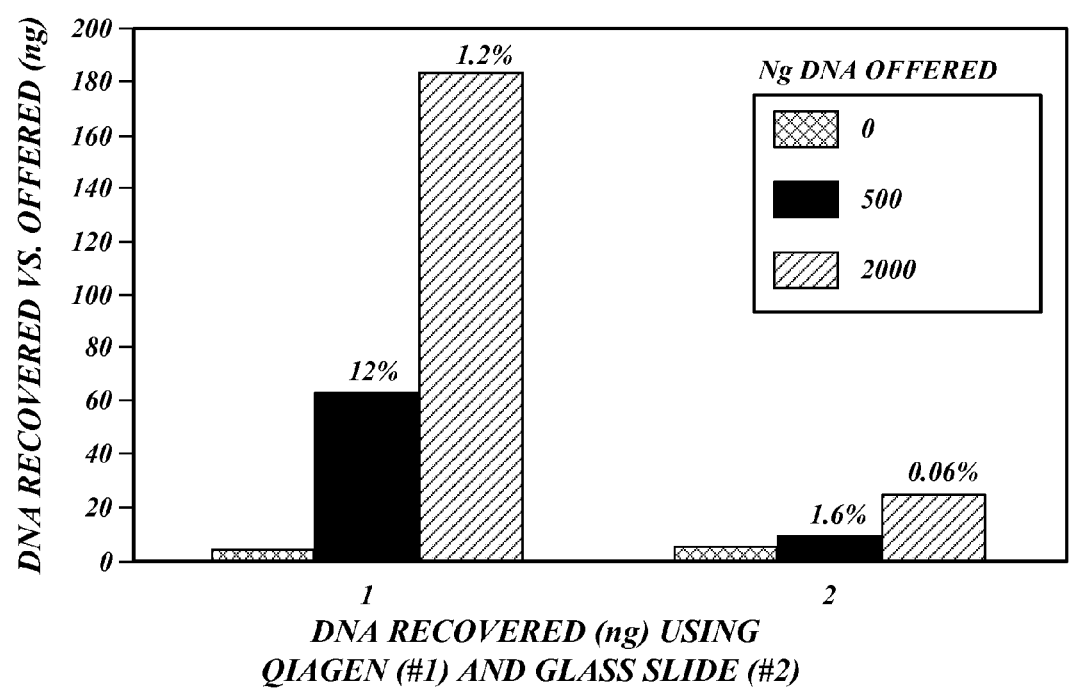
FIG. 9 is a graph comparing the amount of DNA recovered using two different methods.
Figure 10:
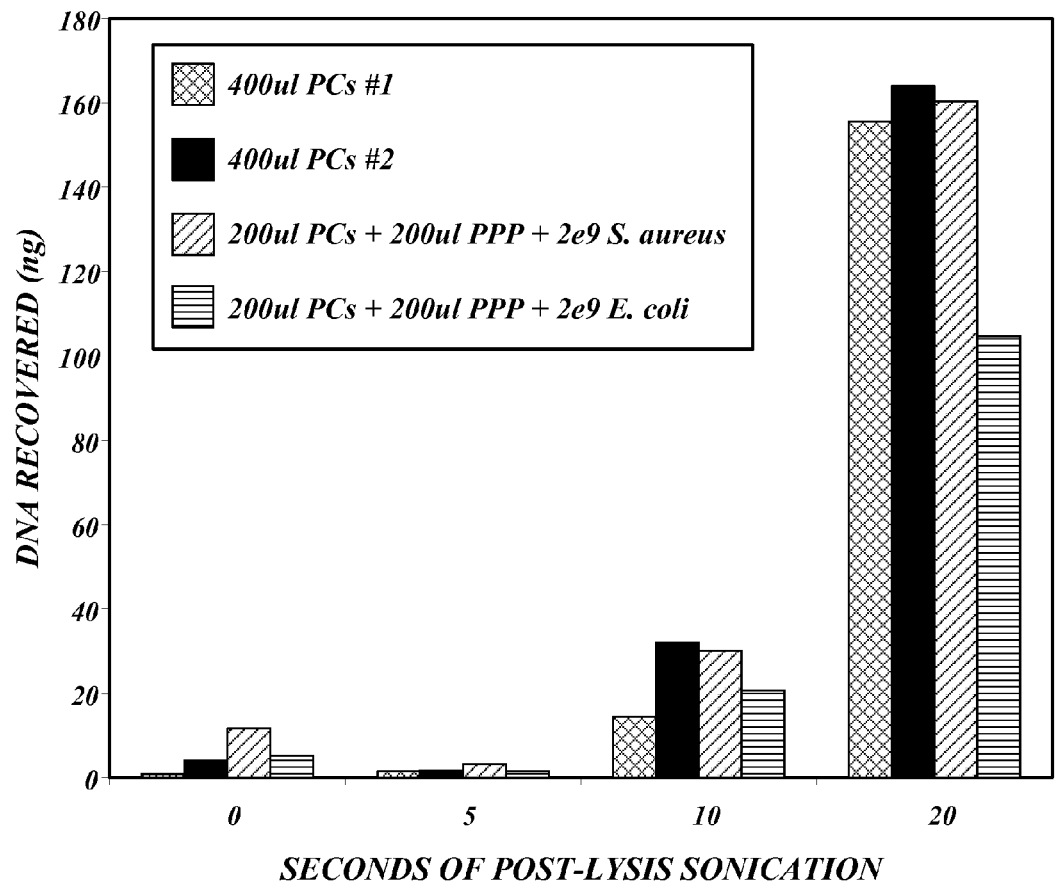
FIG. 10 is a graph comparing the amount of DNA recovered following post-lysis sonication for different types of cell samples.

Because several sources of exogenous nucleic acids found in the biological samples may be recalcitrant to a particular lysis buffer and proteolytic digestion, other methods were developed to carry out more complete lysis of such samples concomitantly or at other points during the preparation. To further demonstrate the inability to recover nucleic acids comprised of genomic DNA efficiently from a complex mixture of bacteria (*Staphylococcus aureus* or *Escherichia coli* at various concentrations) in human plasma and platelet concentrates using the methods described in U.S. Pat. No. 5,234,809, the following experiment was performed. Referring to FIG. 9, the novel combination of heating and of sonic probe sonication of the lysates for various times (from 0-20 seconds) prior to adsorption of the nucleic acid onto the glass slides was performed. The results demonstrate a substantial increase in recovered nucleic acid with increased sonication times. FIGS. 9 and 10 shows the percentage recoveries of such nucleic acids from plasma following the methods taught in the Qiagen Blood Mini Kit and those described herein, and in both cases the recovered amounts are low (<12% of offered).

U.S. Pat. No. 6,235,501 describes a method for the isolation of high molecular weight DNA from biological samples. Controlled oscillatory mechanical energy is applied to the sample for short periods of time (5-60 seconds) to lyse the sample and release the DNA. A spherical particle is used for applying the mechanical energy. In the practice of the present invention, mechanical disruption of the biological sample materials uses a sonicator probe, a piezobuzzer device, or another similar device capable of introducing high frequency resonant vibrations to the sample through a chamber wall of the DNA card. The shearing of DNA in the methods of the invention significantly increases the total amount of DNA released from the sample that is purified from the glass surfaces compared to other methods well known to those who practice in the field of nucleic acid extraction. In addition, to facilitate the lysis and inactivation of pathogenic organisms within the various samples as described above, the sample will also be heated to temperatures up to 95° C. for a period of time of 2-10 minutes in the presence of various combinations of reagents and, if needed, concomitantly with the other disruptive methods such as described above.

Figure 11:
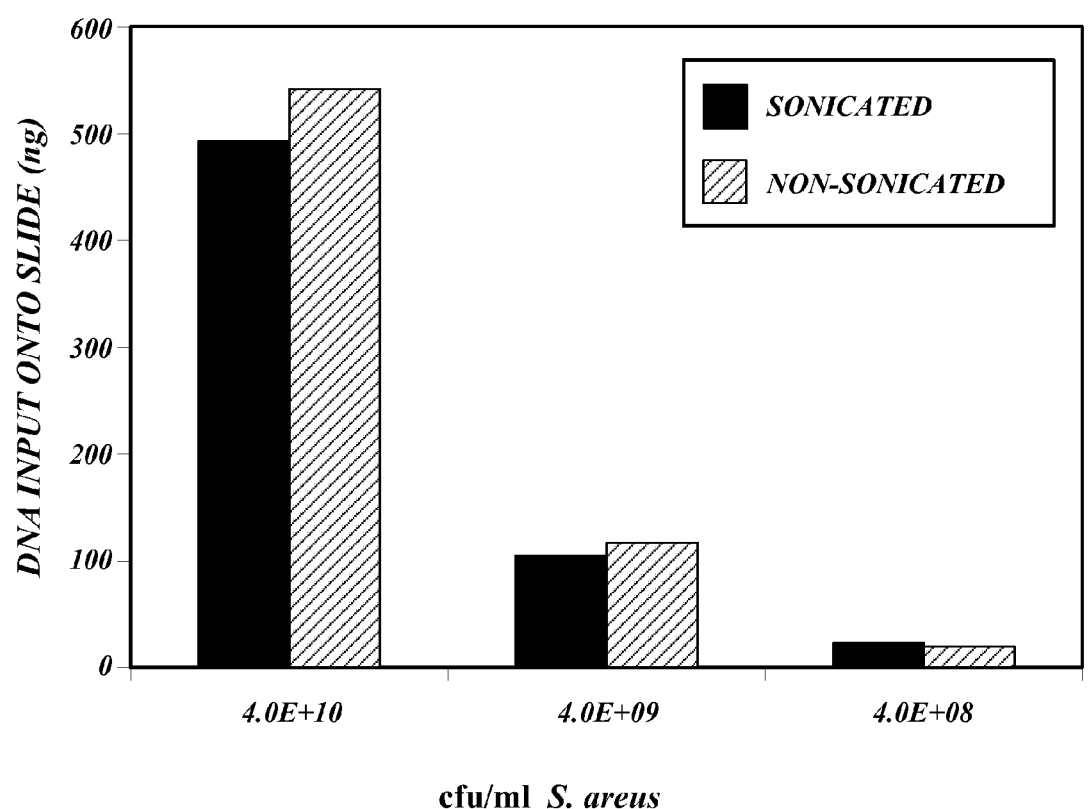
FIG. 11 is a graph comparing the amount of DNA released after lysis from sonicated and unsonicated bacterial cell cultures.
Figure 12:
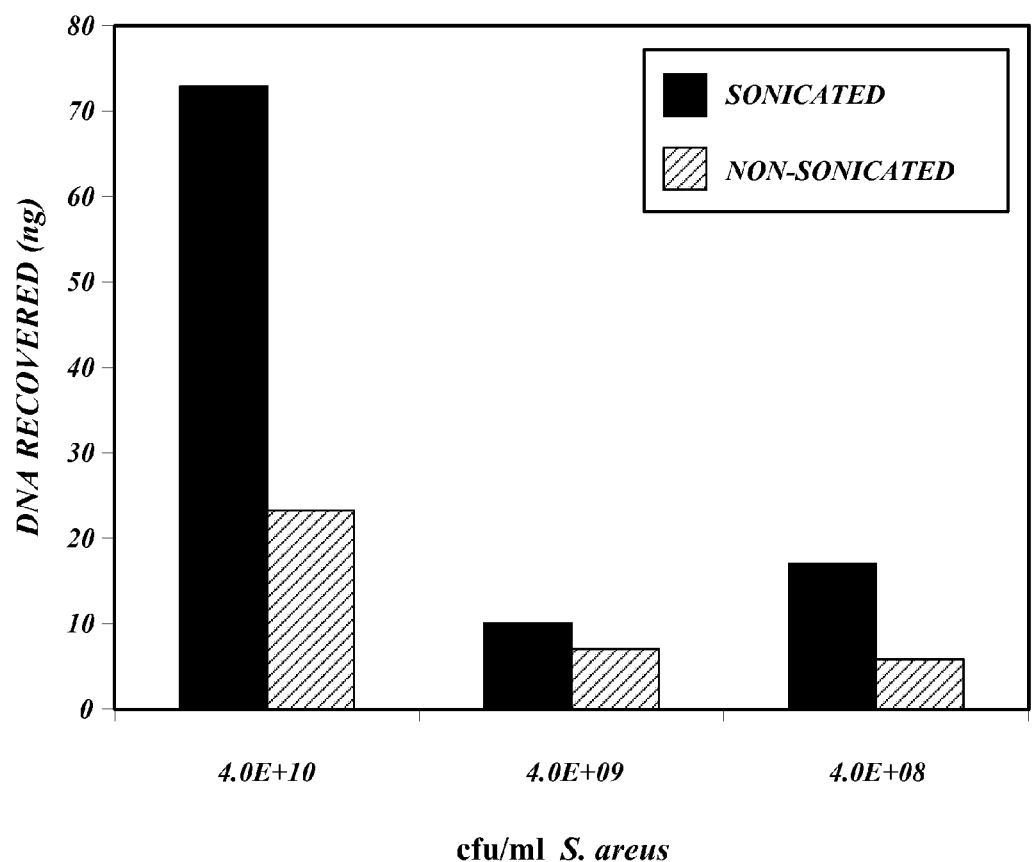
FIG. 12 is a graph comparing the amount of DNA recovered from sonicated and unsonicated bacterial cell cultures using a representative method of the invention.

Referring to FIG. 11, the total input DNA from a complex starting material comprised of lysate was measured after mixing plasma and a known quantity of bacterial cells (*Staphylococcus aureus*). FIG. 11 shows equivalent release of genomic DNA from the samples into each lysate following probe sonication for 90 seconds and the 95° C. 10 minute heating steps. FIG. 12 shows increased recovery of said genomic DNA from the samples following probe sonication for 90 seconds and the heating step as described above using the methods of the present invention.

Figure 13:
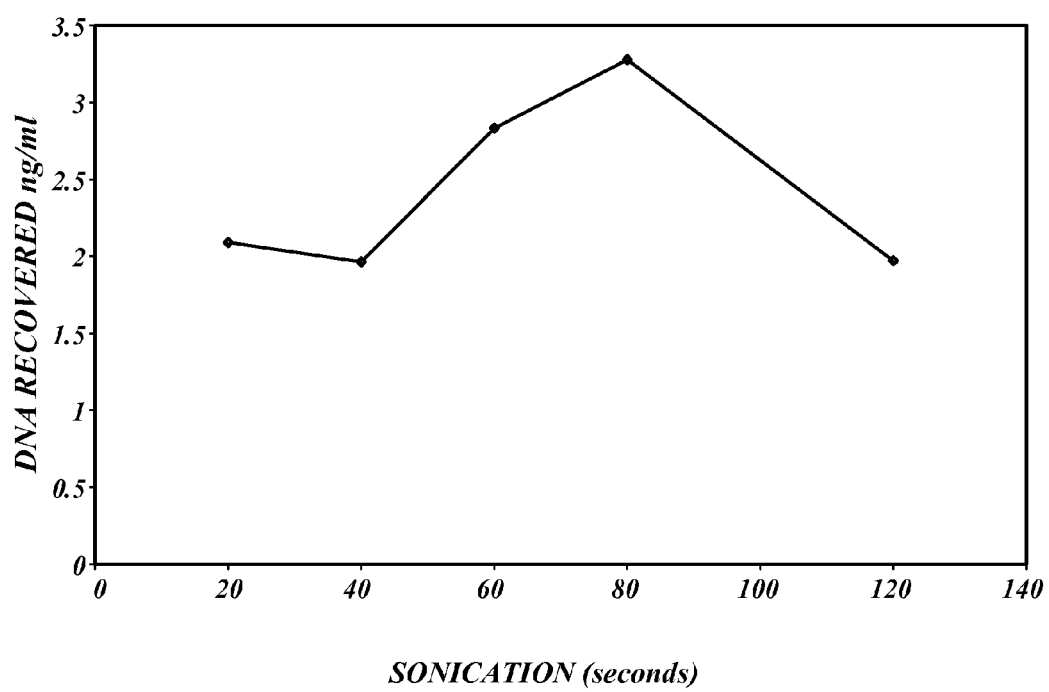
FIG. 13 is a graph showing the amount of DNA recovered following different sonication times.

FIG. 13 is a graph showing the amount of DNA recovered following different sonication times. Referring to FIG. 13, with regard to the level of sonication or similar mechanical disruption needed for the recovery of nucleic acids from biological materials using the protocols described herein, the optimum time of probe sonication at about 350 MHz carried out with a Branson Sonifier on a lysate in an Eppendorf tube was determined in the following experiment. Several samples containing 200 ul of an outdated platelet concentrate were extracted and exposed to various time periods of continuous sonication. For the longer time periods of sonication (>30 seconds) the samples were briefly cooled on an ice slurry following one 30 second pulse. The total DNA recovered from the glass slides following elution is shown in the graph in FIG. 13 as quantified with the PicoGreen assay as per the manufacturer's instructions (Invitrogen Inc.) in a BioTek plate reader using the appropriate filter sets. Based on these results, the time of sonication as carried out with the Branson probe sonicator as described above should normally be about 90 seconds and applied in three separate 30 second pulses.

Figure 14:
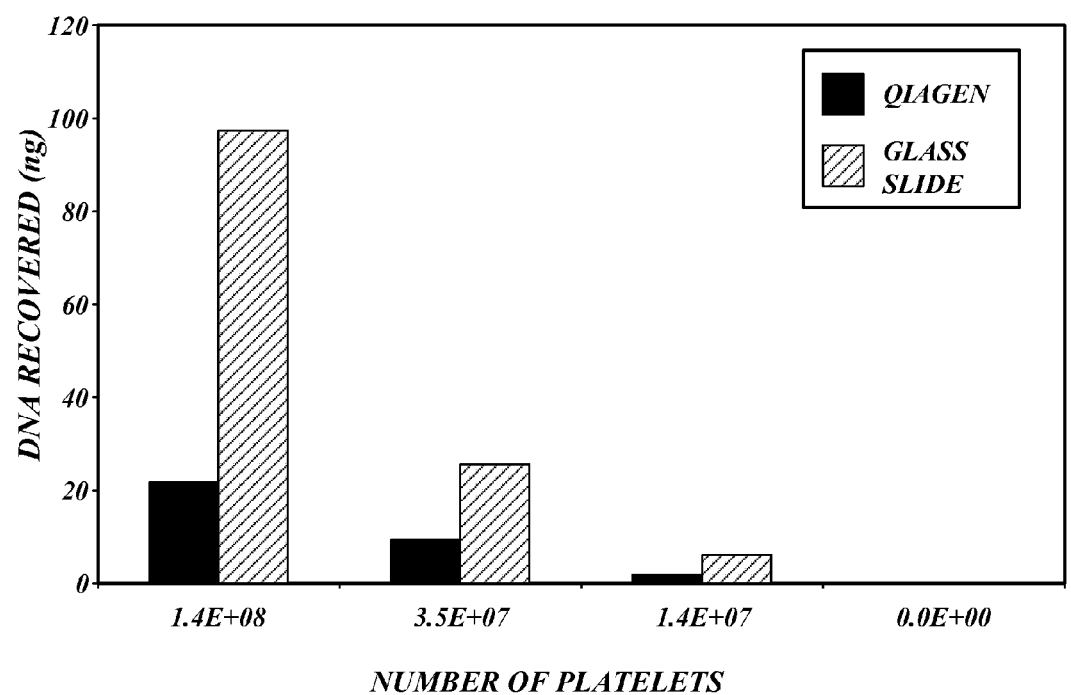
FIG. 14 is a graph comparing the amount of DNA recovered from different concentrations of PCs using two different methods.

FIG. 14 is a graph comparing the amount of DNA recovered from samples containing different PC concentrations using two different methods. Referring to FIG. 14, experiments were conducted to compare the performance of the glass slide purification system with the Qiagen Blood Mini Kit, a commercially available DNA purification system. In this experiment, lysates containing DNA extracted from 200 ul of platelets (prepared as described below) were split evenly and dispersed onto either a Qiagen column or a single glass slide, respectively. For the Qiagen column preparations the samples were then washed with wash buffers 1 and 2, and finally eluted with 200 ul of TE. After 20 minutes of incubation, the slides were washed with wash buffers 1 and 2. DNA was eluted from the glass slides with 200 ul of TE. All samples were quantified using the PicoGreen assay (Invitrogen) as per the manufacturer's instructions. The results of this experiment are shown in FIG. 14.

Figure 15:
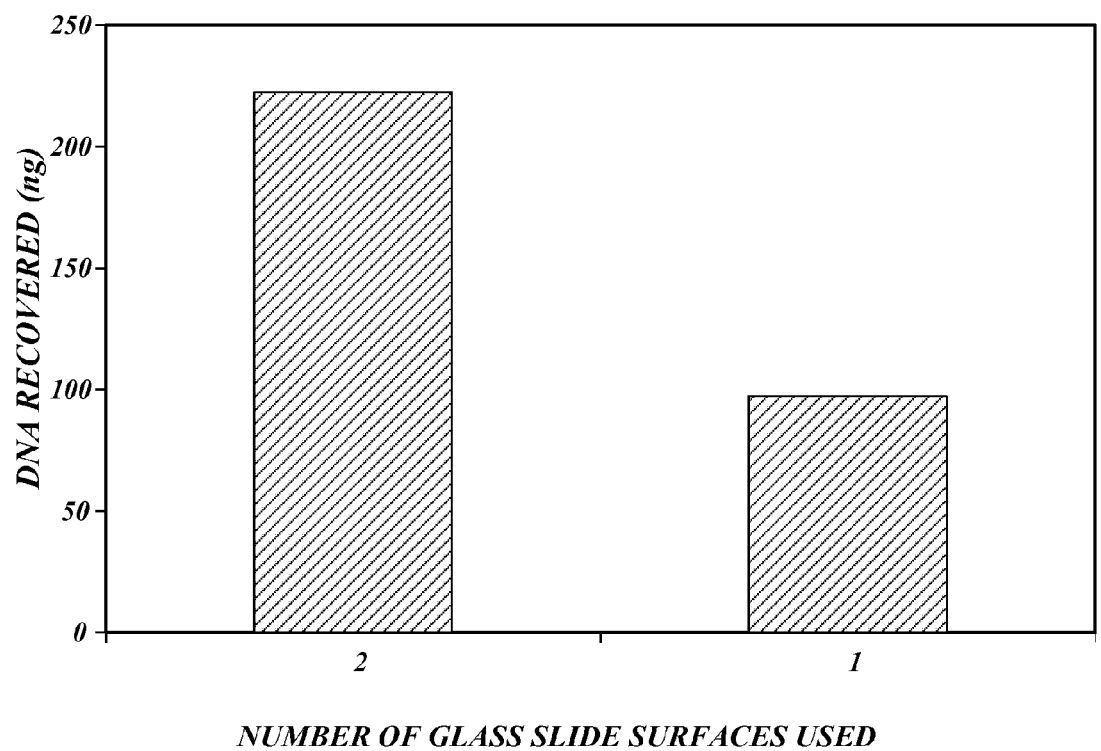
FIG. 15 is a graph comparing the amount of DNA recovered to the number of glass slide surfaces used to isolate DNA using a representative method of the invention.

FIG. 15 is a graph comparing the amount of DNA recovered to the number of glass slide surfaces used to isolate DNA using the method of the invention. Referring to FIG. 15, to demonstrate that the levels of DNA recovered from these samples are directly related to the total area of the glass slides a titration experiment was carried out. Briefly $1.4 \times 10^8$ platelets were collected into 200 ul of plasma and extracted using the protocols described herein using either one single glass slides or two separate glass slides separated by at least 0.417 mm of air space (see example below). The total amounts of DNA recovered following elution at 56° C. for 15 minutes is shown in FIG. 15. The amount of DNA purified from one glass slide is roughly one half of that purified from two glass slides in this experiment demonstrating quantitative recovery of DNA from $1.4 \times 10^8$ platelets. Thus, the surface area of the glass slides used for the purification correlates directly to the total amount of DNA recovered from the lysates obtained using platelet concentrates.

Figure 16:
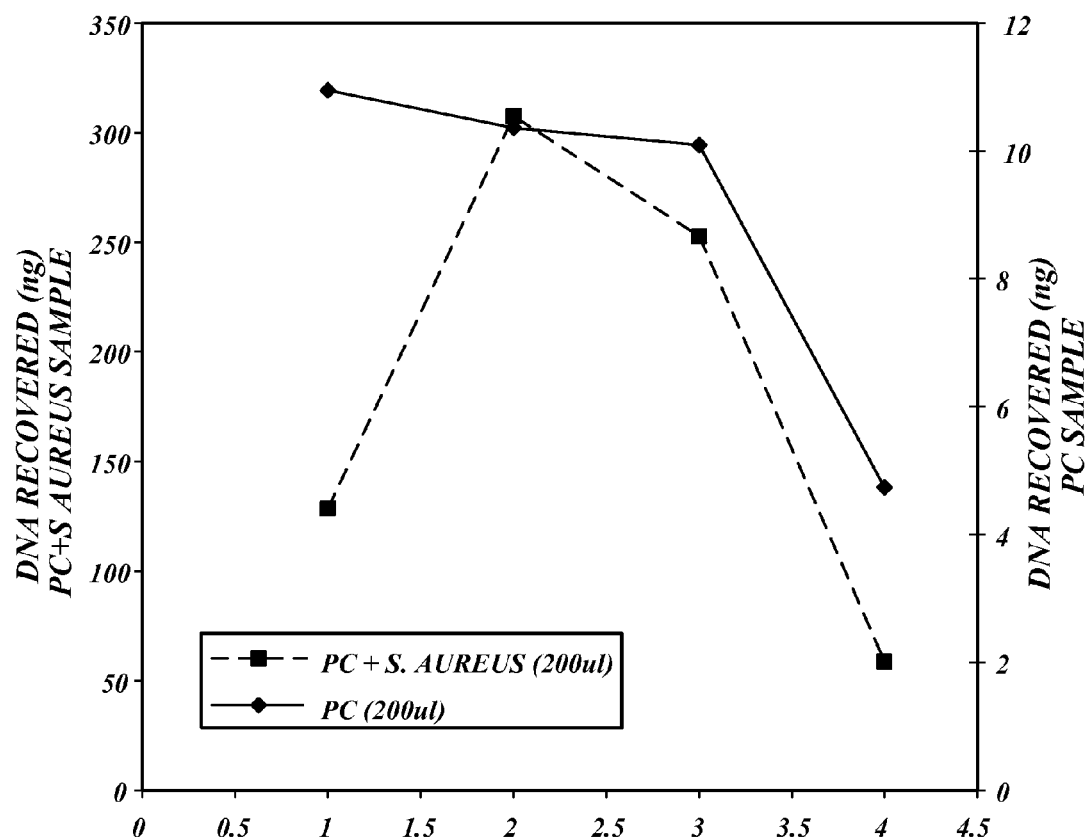
FIG. 16 is a graph comparing the amount of DNA recovered from different samples as a function of the number of slides used to isolate DNA using a representative method of the invention.

FIG. 16 is a graph comparing the amount of DNA recovered from different samples as a function of the number of slides used to isolate DNA using the method of the invention. Referring to FIG. 16, the DNA binding capacity of the glass slides was analyzed using two types of lysates—a relatively DNA rich lysate (PC+*Staphylococcus aureus* as described below) and a relatively DNA poor lysate (PC alone as described below). 200 ul of platelet concentrates in plasma or 200 ul of platelet concentrates in plasma mixed with approximately $1 \times 10^9$ cfu/ml *Staphylococcus aureus* bacterial cells were extracted using the protocols described herein. The total amount of lysate was first dispersed in equal volumes across three sets of superimposed glass slides separated by 0.417 mm of air space (about 200 ul for each set of slides). Subsequently, the total lysate amount recovered from the first three sets of slides (about 600 ul total) was pooled and spread across a fourth set of superimposed glass slides separated by 0.417 mm of air space. The DNA was recovered following overnight elution at room temperature in 200 ul of TE buffer for each paired set of slides was quantified, and normalized to 200 ul volume of lysate for each of the four slide sets. The total amount of recovered DNA from each set of slides in these experiments is shown in FIG. 16. This experiment shows that most of the DNA from the lysates is recovered on the first three sets of glass slides and that the total amount of DNA available for binding to the glass surface is significantly less for the fourth glass slide. Moreover, the equal "levels" of binding of DNA in both types of lysate for the first three slides in the DNA rich versus DNA poor lysates suggests that the glass slides function to bind a fixed percentage of the total DNA available in the lysates that is independent of the total DNA concentration. Efficient recovery of even larger (microgram amounts) of DNA from one set of paired glass slides in other experiments (data not shown) has been observed, suggesting that the binding capacity of glass is larger when using biological materials than those used in these experiments.

Figure 17:
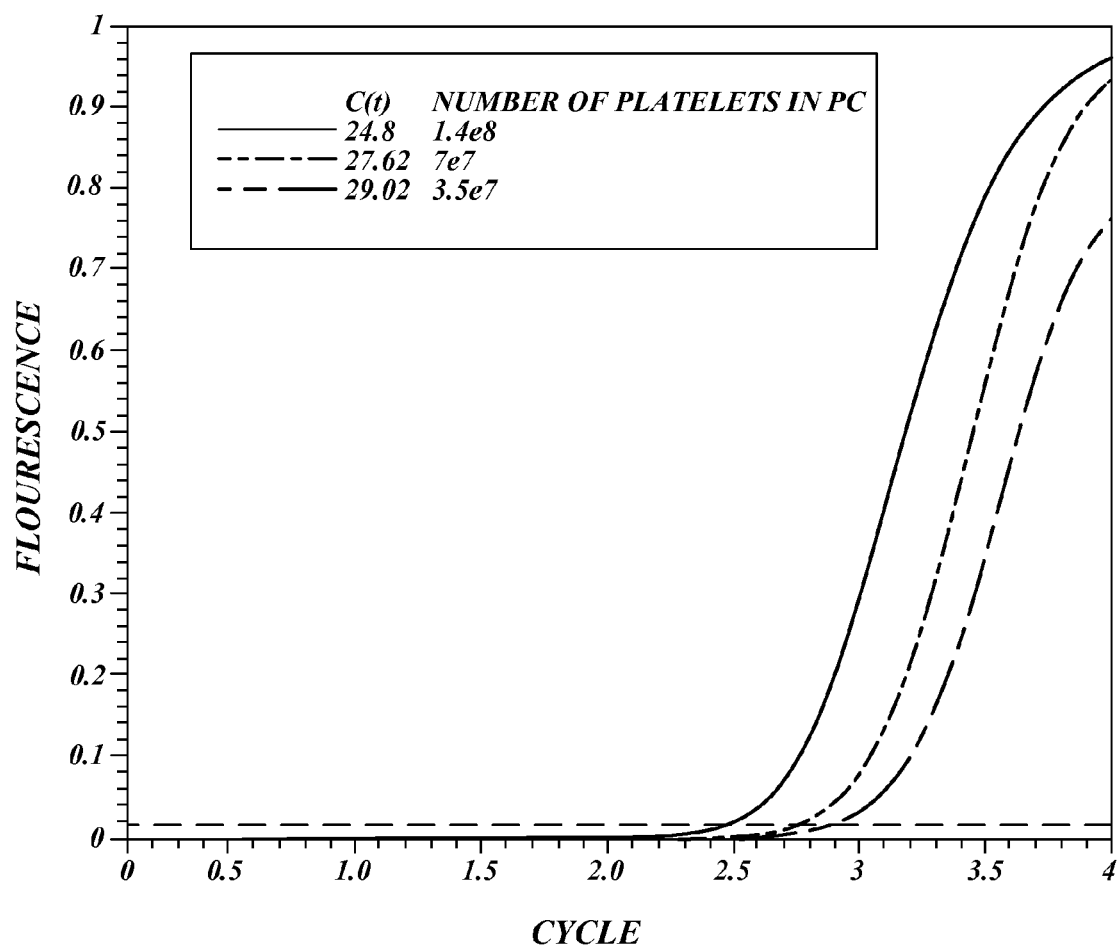
FIG. 17 is a graph showing real-time PCR C(t) values for PC samples with different platelet concentrations.
Figure 18:
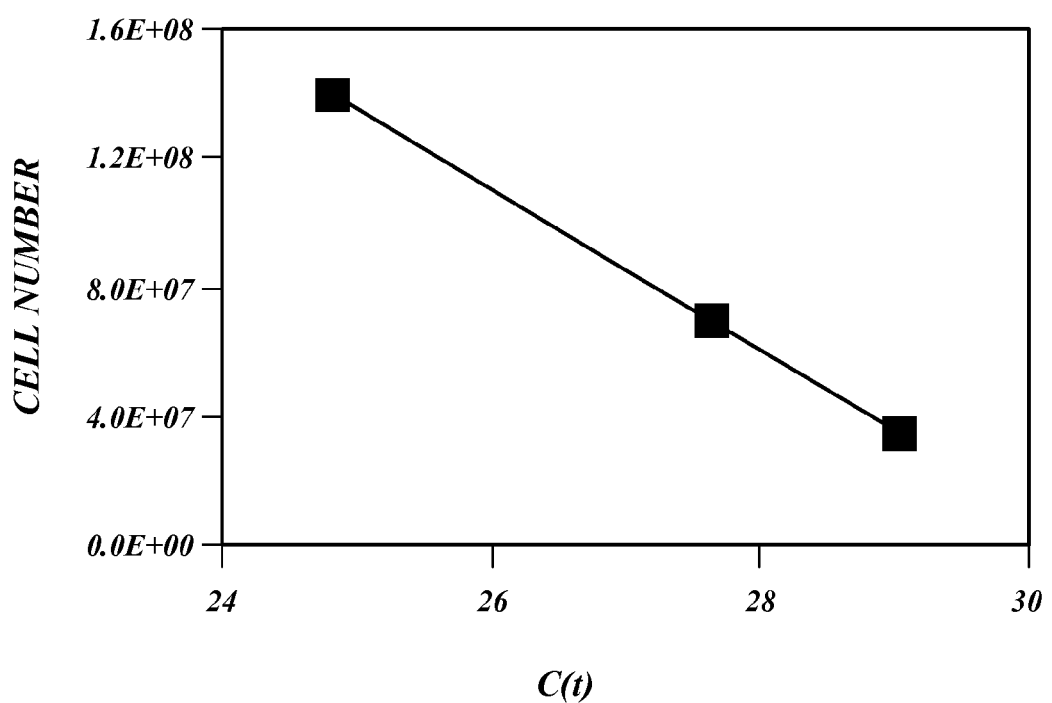
FIG. 18 is a graph showing real-time PCR C(t) values for samples with different platelet concentrations.

To study the quality of the DNA extracted using the method of the invention some of the DNA preparations were analyzed by real-time polymerase chain reaction (RT-PCR) following purification from the glass slides. About one-one hundredth volume of the samples (about 2 ul) prepared from platelets ranging in number from $1.4 \times 10^8$ to $3.5 \times 10^7$ were subjected to real-time PCR using the AmpliTaq Gold LD DNA polymerase (Applied Biosystems) as per manufacturer's instructions, except that Ambion RT-PCR grade water was used throughout all points of the protocol and following purification of all reagents used in the PCR reactions over a YM-100 ultrafiltration column (Millipore Inc.) as per the manufacturer's instructions for samples containing DNA. The PCR reaction was followed in real-time using a MJ Mini Opticon instrument (BioRad Inc.) by including SYBR Green dye (Invitrogen) into each PCR reaction mix at a concentration of 1X(diluted from 10000X stock using Ambion RT-PCR grade water). Amplification of a fragment of the HLA-DQA gene from genomic DNA in leukocytes was carried out using primers as described in Mohammadi et al., "Detection of Bacteria in Platelet Concentrates: Comparison of Broad-Range Real-Time 16s Rdna Polymerase Chain Reaction and Automated Culturing." *Transfusion* 45: 731-736, 2005, incorporated herein by reference in its entirety. This showed that there were no PCR inhibitors in the extracted DNA samples as well as template concentration dependence (as inferred from the various number of platelets and lymphocytes extracted) upon the C(t) values obtained from the reactions in FIG. 17. Threshold cycle C(t) reflects the cycle number at which the fluorescence generated within a reaction crosses the threshold and is inversely correlated to the logarithm of the initial copy number. The C(t) value assigned to a particular well thus reflects the point during the reaction at which a sufficient number of amplicons have accumulated. FIG. 18 graphs the C(t) values obtained versus the concentration of platelets included in each DNA extraction.

Figure 19:
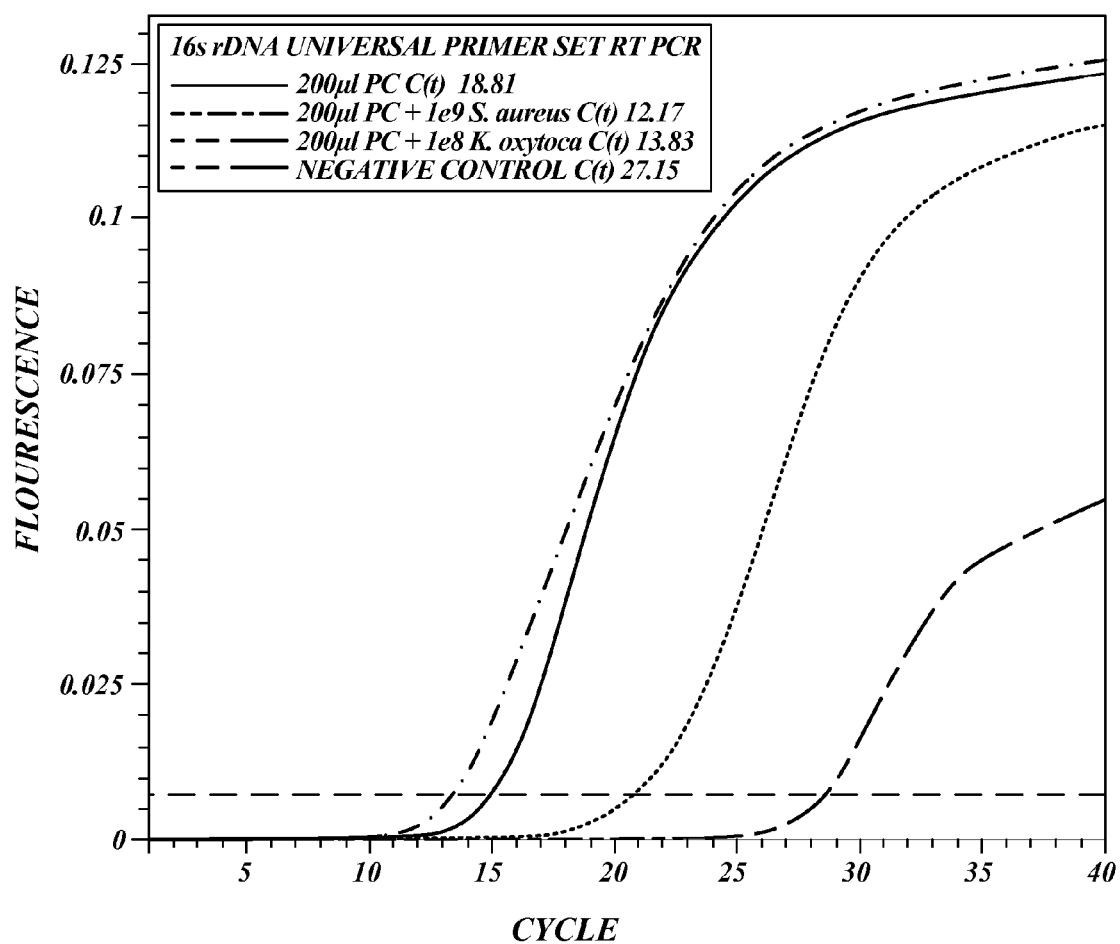
FIG. 19 is a graph showing real-time PCR C(t) values for PC samples with and without bacterial contamination.

Referring to FIG. 19, to demonstrate that the quality of the DNA extracted using the methods of the present invention are of sufficient quality to allow detection of bacterial DNA in platelet concentrates (PCs) some of the DNA preparations prepared on PCs contaminated with *Staphylococcus aureus* or *Escherichia coli* bacteria were analyzed by real-time polymerase chain reaction (RT-PCR) following purification from the glass slides. About one-one hundredth volume of the samples (about 2 ul) prepared from platelets and bacteria containing about $1\times10^9$ cfu/ml of each type of bacteria were subjected to RT PCR using the AmpliTaq Gold LD DNA polymerase (Applied Biosystems) as per manufacturer's instructions except that Ambion RT-PCR grade water was used throughout all points of the protocol and following purification of all reagents used in the PCR reactions over a YM-100 ultrafiltration column (Millipore Inc.) as per the manufacturer's instructions for samples containing DNA. The PCR reaction was followed in real-time using a MJ Mini Opticon instrument (BioRad Inc.) by including SYBR Green dye (Invitrogen) into each PCR reaction mix at a concentration of 1X(diluted from 10000X stock using Ambion RT-PCR grade water). Amplification of a fragment of the 16S rRNA gene from genomic DNA in bacteria was carried out using the universal 16S rRNA primers as described in Mohammadi et al., "Detection of Bacteria in Platelet Concentrates: Comparison of Broad-Range Real-Time 16s Rdna Polymerase Chain Reaction and Automated Culturing." *Transfusion* 45: 731-736, 2005, and is depicted in the graphs in FIG. 19.

Immobilized minor groove binders (e.g., bis-benzimide or BB dyes) can be used to detect DNA in a chamber of the device of the invention. BB dyes have unique properties that may have advantages in PCR detection. The blue fluorescence of the DNA bound BB dye (460 nm) is not read on current commercial thermal cycling fluorimeters, but can be read on a separate channel or in a separate instrument. This allows the DNA concentration to be measured inside the card if BB dye is added to the elution buffer. The presence of the BB dye does not significantly affect the reading of the standard green (520 nm) to red (650 nm) fluorescent dye used to quantify amplified nucleic acids. In one aspect of the invention, a BB dye as a bulk DNA detecting dye is used to provide additional control of the DNA extraction process. NAT reagents (primers, dNTPs, Taq polymerase) can be added to the elution buffer allowing for DNA amplification to take place in the vessel of the invention. When a BB dye is also present in the PCR mix, it can also be used to detect the presence of amplified DNA.

As noted above, in one aspect, the invention provides methods for extracting and quantitating nucleic acids from biological samples, such as blood and blood products, for the purpose of determining the presence of microbial contaminants in the sample. In another aspect, the invention provides methods that utilize the nucleic acid extraction method and further amplify the extracted nucleic acids to provide for the identification of the amplified nucleic acids.

Automated techniques for use of PCR on blood samples generally require tedious DNA extraction protocols to remove interfering substances in the plasma. The DNA extractions can use automated liquid handling systems that are expensive and difficult to maintain. In one aspect, the invention provides a "lab-on-a-chip" device that combines cellular lysis, DNA extraction and purification, and measurement of extracted DNA. A representative device of the invention is illustrated in FIGS. 1 and 20-22 and described in detail below. The device of the invention is a vessel for receiving and processing a biological sample as described above, and because of its structure and form (e.g., in one embodiment a nine-layer laminate, see FIGS. 20A and 20B) is also referred to herein as a "card." The device allows sample entry, digestion, and DNA purification to take place inside a closed vessel that allows the lysis, binding and wash buffers to be delivered in a controlled fashion (aseptic sampling and handling). After capture in the purification chamber of the device, the extracted and processed DNA can remain inside the closed card for storage until ready for NAT.

In one embodiment of the method of the invention, the extracted DNA is eluted from the card using an elution buffer and transferred to a commercially available thermal cycling fluorimeter for quantitative analysis of the DNA by PCR.

In another embodiment, fluorogenic DNA binding dyes can be added to the elution buffer to measure the amount of purified DNA. The device of the invention includes a window that allows for the determination of the quantity of purified DNA by fluorescence. The window allows for excitation of the dyes and measurement of their emission to provide a quantitation of purified DNA. The inclusion of a blue fluorescent dye (e.g., a bis-benzimide, BB, having emission maximum at about 460 nm) in the elution buffer allows the quantitation of extracted double stranded DNA (dsDNA) prior to NAT. The method provides a positive control for the DNA extraction process. Other conventional fluorescent materials (green, yellow, orange, red emissions) can be used with standard DNA probe technology to detect primer directed amplification of target DNA fragments in real time.

To study utilize the blue fluorescent dye in real time PCR, a UV excitation source/blue fluorescence detector instrument is required. A suitable instrument is a thermal cycling fluorimeter having an LED/photodiode-based optical platform (BioRad Mini-Opticon). In practice, a filter set for SYBR green (DNA-bound form Ex=490 nm, Em=520 nm), the commercial standard for DNA detecting fluorescent dyes, was used.

The Mini-Opticon system noted above worked well for a PCR assay using the lymphocyte gene HLA-DQA1. Amplification of a fragment of the HLA-DQA gene from genomic DNA in leukocytes was carried out using primers as described in Mohammadi et al., "Detection of Bacteria in Platelet Concentrates: Comparison of Broad-Range Real-Time 16s Rdna Polymerase Chain Reaction and Automated Culturing." *Transfusion* 45: 731-736, 2005. The results of the assay showed that there were no PCR inhibitors in the extracted DNA samples using the glass slide method of the invention. As expected, C(t) values increased with decreasing template concentration. The Mini-Opticon cannot be easily adapted to read both green and blue fluorescence.

A second suitable thermal cycling fluorimeter is commercially available from BioRad under the designation Chromo4. The fluorimeter houses a customized photonics shuttle that moves an LED/photodiode housing to various positions over a 96-well plate.

In practice, the shuttle includes a UV-LED light source and suitable filters (Ex=360 nm, Em=460 nm). Commercially available UV-LED sources have ideal wavelength for excitation of the BB dye. In one embodiment, the invention provides a thermal cycling fluorimeter capable of both green (labeled probe for amplified nucleic acid quantitation) and blue (dye for extracted nucleic acid quantitation) emission detection.

Thus, in another aspect of the invention, a method for amplifying and quantifying the amount of nucleic acids in a sample is provided. In one embodiment, the method includes:

(a) introducing a sample containing cells in a liquid medium into a first chamber of a vessel, the vessel comprising the first chamber and a second chamber, wherein the first chamber is in liquid communication with the second chamber and wherein the second chamber has at least a portion of one surface effective for binding nucleic acids;

(b) lysing the cells to provide nucleic acids in the liquid medium;

(c) transferring at least a portion of the liquid medium from the first chamber into the second chamber;

(d) extracting the nucleic acids from the liquid medium by binding the nucleic acids to a surface of the second chamber effective for binding nucleic acids, to provide isolated nucleic acids;

(e) releasing the isolated nucleic acids from the surface of the second chamber effective for binding nucleic acids by contacting the isolated nucleic acids with a buffer solution;

(f) treating the isolated nucleic acids with a nucleic acid amplification reaction mixture under conditions for amplifying the isolated nucleic acids to provide amplified nucleic acids;

(g) contacting the amplified nucleic acids with a fluorescent compound having a fluorescence intensity dependent on the concentration of nucleic acids; and (h) measuring the fluorescence of the fluorescent compound to determine the quantity of amplified nucleic acids. In one embodiment the method includes repeating steps (f) and (h) a pre-determined number of times to determine the amount of amplified nucleic acids.

In another embodiment, the method includes contacting the isolated nucleic acids with a fluorescent compound having a fluorescence intensity dependent on the concentration of nucleic acids and measuring the fluorescence of the fluorescent compound to determine the quantity of isolated nucleic acids prior to step (f).

In one embodiment, the fluorescent compound is immobilized in the second chamber. The fluorescent compound can be immobilized in the device as one or more patches of a film that can be adhered inside the second chamber (e.g., the serpentine-shaped chamber or S-channel, see FIG. 1, reference numeral 400). Through the use of films of immobilized fluorescent compounds, concentrations of DNA-detecting dye to be readily adjusted.

The immobilization chemistry used to attach a representative DNA-sensing material (e.g., BB-NH$_2$) to the glass slide surface can be varied. In one embodiment, the DNA-sensing material is attached to human serum albumin (HSA) as a biocompatible linker to provide a sensor film. Albumin is often used to coat surfaces to prevent DNA from adhering to them, a desirable feature in the sensor film. In one embodiment, a BB-NH$_2$ dye is coupled to HSA in various dye to protein ratios via the carboxyl groups on the aspartic acid residues. Alternatively, an electrophilic form of the BB dye (such as the cyanuric acid derivative) can be attached to the HSA via the lysine residues. The ability of BB-HSA (in solution) to quantitate dsDNA can be optimized (loading levels, linker type). The fluorophore/protein linkers and loading level can be tuned for fluorescent signal and dynamic range of response.

Figure 23:
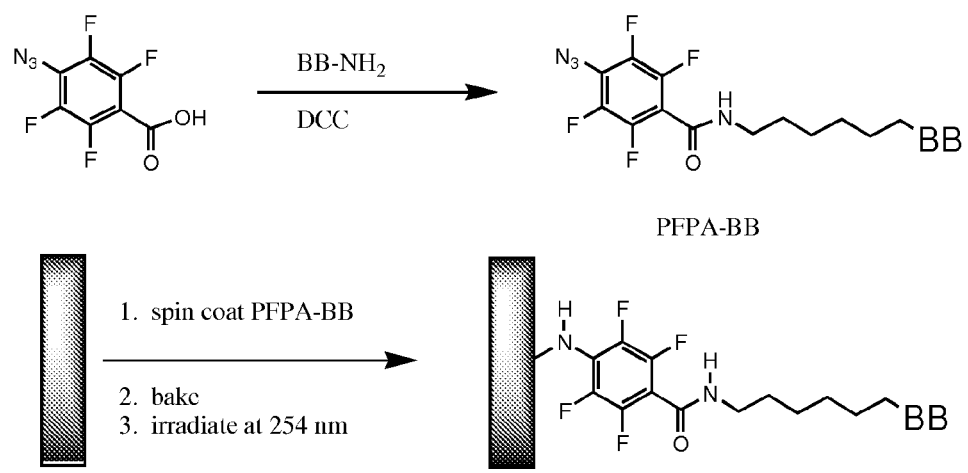
FIG. 23 illustrates a representative method for covalently coupling a DNA-sensing material to a polymeric substrate.

Non-porous polymeric surfaces functionalized with NHS ester groups may also be used for attaching the DNA-sensing material to provide the DNA sensing film. In this embodiment, the surface of non-porous polymeric substrates can be directly functionalized for use in the DNA sensor film. In one embodiment, the substrate includes a polymeric polyethylene glycol (PEG) surface. Various linkers can be introduced to the starting BB-NH2 dye by simple amide coupling chemistry. FIG. 23 illustrates a representative method for covalently coupling a DNA-sensing material to a polymeric substrate.

As shown in FIG. 23, the CH insertion of the photoactivated nitrene intermediate is adaptable to various polymeric substrates to provide various thin film materials. Suitable substrates include polypropylene and PVC, each having low binding to DNA.

Referring to FIG. 23, a derivative of the BB fluor that is photoactivatable (PFPA-BB) is used for direct immobilization to polymeric substrates. In one embodiment, hydrophilic PEG linkers are included intermediate the PFPA and the BB fluor to allow conformational flexibility of the BB dye and improve DNA binding efficiency.

In one embodiment of the immobilized DNA-sensing material, the sensor substrate includes a PFPA derivative of biotin with a PEG linker coated on a polymer film, irradiated at 254 nm, and washed. The amount of surface bound biotin can be measured by treating with tetramethylrhodamine (TAMRA) labeled streptavidin (SA). Excess TAMRA-SA is washed off to measure 550 nm fluorescence of the biotin-SA complex.

In another embodiment, the DNA-sensing material is not immobilized, but rather introduced into the device of the invention so as to contact the nucleic acids to be quantified. In one embodiment, the nucleic acid amplification mixture includes a fluorescent compound.

In yet another embodiment, the buffer solution comprises the fluorescent compound and the nucleic acid amplification reaction mixture.

In the methods above, the fluorescent compound is a minor groove binder or an intercalating agent. In one embodiment, the fluorescent compound is a bis-benzimide (BB) compound (e.g., BB derivative).

In one embodiment, the method further includes determining the presence of a gene or gene product in the sample by the presence of amplified nucleic acids. As used herein, nucleic acid amplification reaction mixture refers to a mixture containing the components necessary for amplifying nucleic acids by PCR. In general, the nucleic acid amplification reaction mixture contains one or more primers that are complementary to the DNA region at the 5' and 3' end of the DNA region that is to be amplified; a DNA polymerase such as Taq polymerase; deoxynucleotide triphosphates (dNTPs); buffer solution; divalent cations such as magnesium ($Mg^{2+}$) or manganese ($Mn^{2+}$) ion; and monovalent cations such as potassium ($K^+$) ions. The term "amplified nucleic acids" refers to nucleic acids produced in the method during the nucleic acid amplification step by reaction of the isolated nucleic acids with the nucleic acid amplification reaction mixture (e.g., by PCR).

The method may also include identifying a type of a gene or gene product in a sample by the presence of amplified nucleic acids. In these methods, specific nucleic acid probes that identify the gene or gene product are used. These probes are labeled with fluorescent compounds and the specific gene or gene product is identified by fluorescence measurement.

In one embodiment, conditions for amplifying the isolated nucleic acids are those of a polymerase chain reaction (PCR). In one embodiment of the method, the isolated nucleic acids are transported from a proximal end of the second chamber to a distal end of the second chamber, the proximal end having a first temperature zone and the distal end having a second temperature zone. The first temperature zone is at about 65° C. and the second temperature zone is at about 95° C. See, for example, FIGS. 22A and 22B.

When NAT reagents (e.g., PCR primers, Taq polymerase, dNTPs) are added to the elution buffer, then analysis of specific genetic sequences can be detected in the card by thermal cycling. Isothermal DNA or RNA amplification methods such as transcription-mediated amplification (TMA) can also be used in the methods of the invention.

For the methods of the invention that include nucleic acid amplification, conventional reagents and buffers are used. Suitable reagents are purified of endogenous and exogenous nucleic acid contamination using one of several well known methods. It is well known that bacterial nucleic acids can contaminate aqueous solutions and that small fragments of DNA can pass through 0.2 um filters used to remove contaminants. The magnitude of contamination when carrying out broad-range rDNA PCR is highly variable and may be overestimated. False positives are minimized by the methods and device of the invention. Taq polymerase can be contaminated with nucleic acids from the bacterial species used for its manufacture. Ultrafiltration of aqueous reagents are suitable for purification reagents useful in the methods of the invention.

For extraction and elution of nucleic acids in the methods of the invention, extraction and elution reagents and buffers are used. These include lysis buffer, proteinase K (or another protease), ethanol, Wash 1 buffer, Wash 2 buffer, Elution buffer (+/−BB-NH2 dye) (+/−SYBR green), as described below.

For the methods of the invention that include nucleic acid amplification by PCR, conventional PCR reagents and buffers are used. Suitable PCR reagents include master mix including $Mg^{2+}$ containing buffer, NTPs, Taq polymerase, 16S rRNA gene primers, 16S rRNA gene probe (FAM label), HLA-DQA1primers, HLA DQA1probe (VIC label).

The methods and device of the invention can be used for quantitative PCR. The use of a blue fluorescent compound having a fluorescent intensity dependent on nucleic acid concentration (e.g., in the S-channel of the device) provides quality assurance of effective sample acquisition and lysis. The inclusion of two temperature zones to the distal ends of the glass walled S-channel allows for quantitative PCR in the device. See, for example, FIGS. 22A and 22B, reference numerals 700 and 800.

Figure 22A:
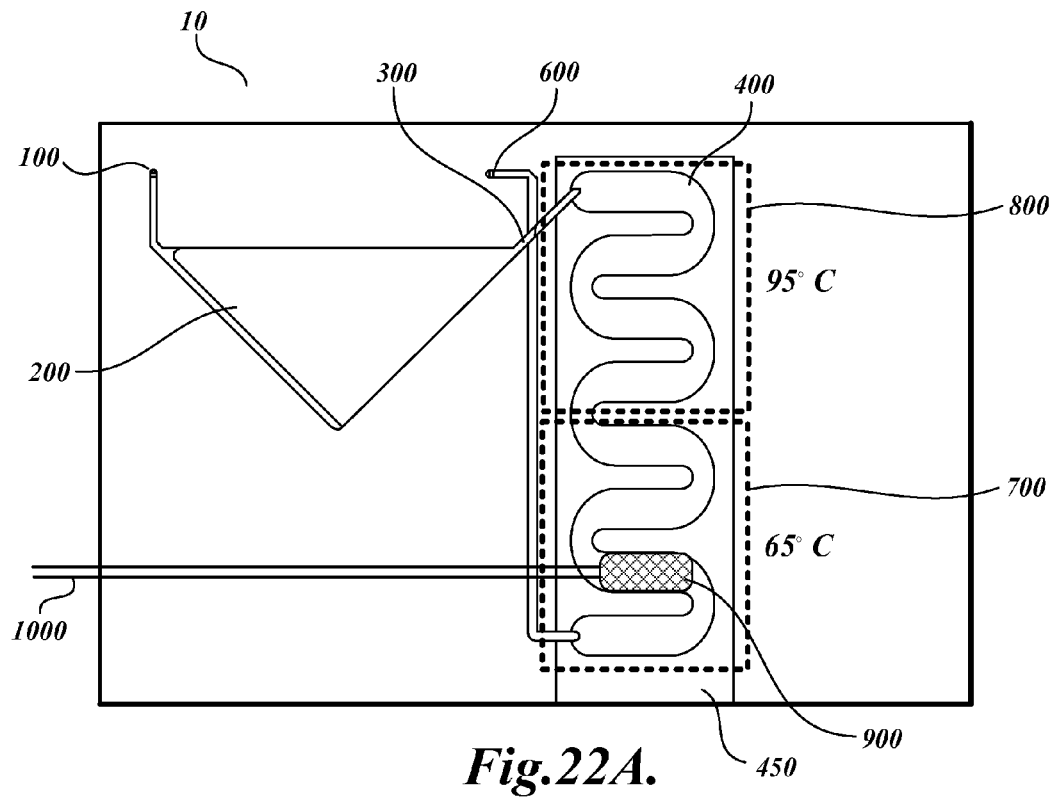
FIGS. 22A and 22B are schematic illustrations of a representative device and method of the invention.
Figure 22B:
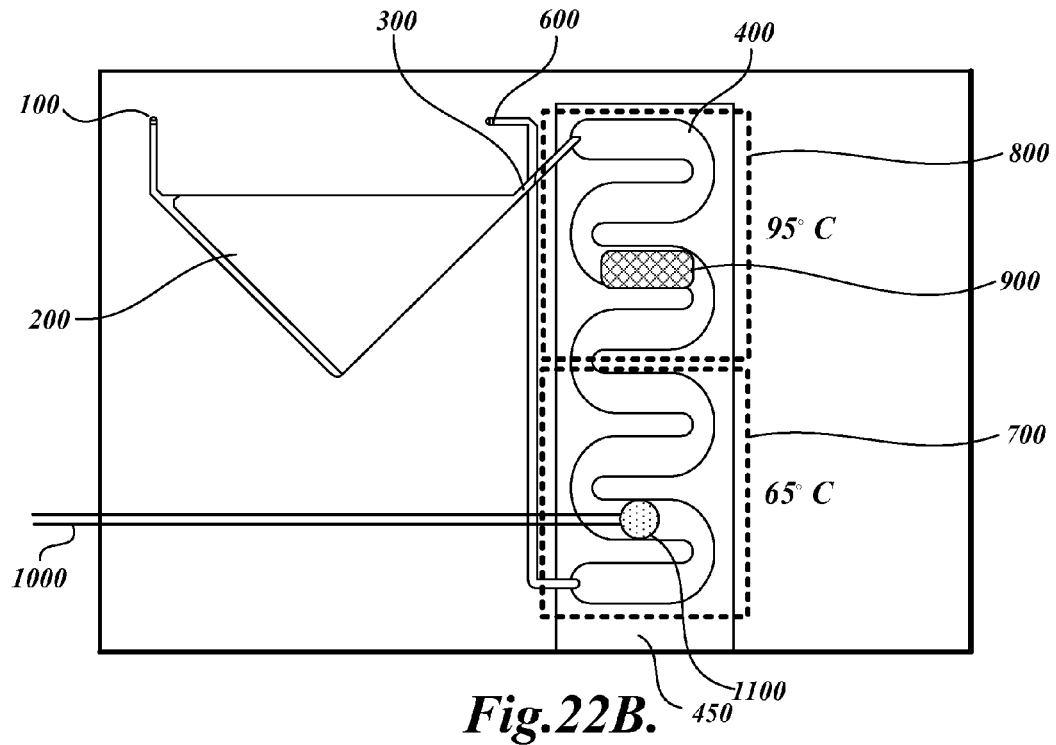

In practice, a PCR master mix with the appropriate fluorescent probe(s) and primers is added to the extracted DNA and the PCR mix (900 in FIGS. 22A and 22B) is pumped back and forth between the two temperature zones (700 and 800 in FIGS. 22A and 22B). The method of the invention provides for cycling of the PCR reaction mixture between the two temperature zones and allows for rapid PCR. Heat transfer into the thin film of the PCR mixture (900) will be rapid as the mixture enters a each temperature zone. A variety of fluorimeters can be utilized in the method and system.

As depicted in FIGS. 22A and 22B, a representative device can include at least two constant temperature zones (700 and 800). Alternatively, the entire device can be subject to rapid cycling temperature of the small and well insulated device.

The relatively small thermal mass of the PCR mix means that it will rapidly change temperature when moved from the lower to high temperature zone. The lower temperature (700, about 65° C.) zone will act as a heat sink for the mixture after being pumped from the high temperature (800, about 95° C.) zone. If the surrounding insulation prevents excess heat transfer from the high to low zone, then again resistive heaters may be employed. Without a means to remove heat from the lower temperature region, heat transfer through the continuous glass slides can raise the 65° C. temperature zone above annealing temperature. Therefore, in one embodiment, the low temperature heat source is a thermoelectric cooling device.

The device includes an optical path for the fluorometric quantitation of nucleic acids. In one embodiment, the optical path includes a UV-LED on one side of the chamber and the 460 nm filter/photodiode on the other side. The power/pulsing of the LED and the gain on the photodiode can be adjusted. Fluorescent signal is collected periodically to determine the position of DNA-sensing material (e.g., BB) in the device and to measure increase in DNA-dependent fluorescence as correlated with cycle number. The data for fluorescence and cycle number is collected on a computer and processed for q-PCR analysis. In one embodiment, the optical path includes the use of a probe (multiple fiber bundle including excitation and emission carrying fibers) that interrogates the PCR mix through a window in the device (see FIG. 22B, reference numerals 1000 and 1100).

In certain embodiments, the methods include the use of a dye (e.g., blue emission) to quantitate extracted and isolated DNA prior to amplification. In one embodiment, the nucleic acid amplification reaction mixture includes a first fluorescent compound having a fluorescence intensity dependent on the concentration of isolated nucleic acids and a second fluorescent compound having a fluorescence intensity dependent on the concentration of amplified nucleic acids. The first fluorescent compound may be a minor groove binder or an intercalating agent, and the second fluorescent compound may be an oligonucleotide probe specific for a first gene or gene product.

The above methods, the nucleic acid amplification reaction mixture may also include a third fluorescent compound having a fluorescence intensity dependent on the concentration of amplified nucleic acids. In one embodiment, the third fluorescent compound is an oligonucleotide probe specific for a second gene or gene product.

The methods noted above multiprobe PCR methods that are useful for simultaneously detecting and speciating bacteria in clinical specimens (e.g., PRP).

Representative fluorimeters useful in eliciting and measuring fluorescence in accordance with the methods and devices of the invention include commercially available instruments including the Bio-Tek Plate Reader (end-point assays on a fluorescent plate reader using an automated protocol and uniform reagents); the Ocean Optics (OO) fiber optic fluorimeter (equipped with a UV-LED available from Nichia (Japan) as the excitation source having 360 nm emission that is an excellent spectral overlap for excitation of the bis-benzimide dyes); and Blood Cell Storage Inc.'s two-color fiber optic fluorimeter (Seattle, Wash.), described in WO 06/023725, expressly incorporated herein by reference in its entirety. Two-color PCR with this device includes a fiber optic bundle and may be optionally configured with an LED on one side of the card and a filtered photodiode on the other. The advantage of either optical configuration is the ability to optimize LED light sources and filters for each different DNA probe color of interest; reader filters (Ex=528 nm, Em=568 nm and 600 nm) have excellent spectral discrimination for commercially available fluorescent DNA probes such as Yakima Yellow (Em=550 nm) and Redmond Red (Em=600 nm) commercially available from Glen Research.

In the above methods the sample may be blood or a blood product (e.g., PRP).

In another aspect of the invention, a fluidic system including a vessel is provided.

The vessel includes:
(a) a fluid inlet port;
(b) a first chamber in fluid communication with the inlet port;
(c) a second chamber in fluid communication with the first chamber, wherein the second chamber has at least one glass surface;
(d) a first channel that connects the first chamber and the second chamber;
(e) a fluid outlet port; and
(f) a second channel that connects the second chamber to the fluid outlet port.

In one embodiment, the second chamber includes two glass surfaces (i.e., top and bottom). See FIGS. 1 and 20-22 illustrating a representative vessel of the invention, (reference numeral 450 refers to the glass surface of second chamber 400).

The use of large glass surfaces for efficient capture of genomic DNA appears to have advantages over finely divided silica particles. Other high surface area glass materials (membranes, diatomaceous earth, powdered glass, silica gel) have been used to get better DNA binding efficiency. Although the DNA binding efficiency is high with these materials, the long DNA molecules get entrained in the silica and recovery can be low. The resulting DNA is sheared during the processing steps (vortexing) and these DNA fragments are recovered. Flat glass surfaces, however, are efficient for capture of small amounts of DNA from dilute samples.

The vessel is preferably made from materials that exhibit low autofluorescence and very low binding of DNA. Representative materials include acrylic, polycarbonate, polypropylene, and polyvinylchloride, but not polystyrene. The materials should also be impervious to ethanol. Suitable materials include polypropylene (a low surface energy thin film); polyester terephthalate (PET); cast acrylic (a high molecular-weight rigid material); 300LSE adhesive film (3M); 467MP adhesive film (3M); and Transil silicone adhesive film.

Suitable glass materials for the vessel include glass available in standard slide (25×75 mm) and cover slip (20 mm or 25 mm squares) and Borofloat (i.e., Pyrex) available in a variety of sizes: 100, 125, 150, 200 mm diameter by 0.5 mm thick disks, 25, 50, 100, 150 mm squares by 0.5 mm thick.

In one embodiment, the system include a pumping means. The pumping means can be effective for transporting fluids through the second chamber. The pumping means can also be effective for transporting fluids from the inlet port to the fluid outlet port. With pumping a 20-200 ul bead of elution buffer or water travels and down the S-channel to collect the DNA after purification at a temperature between 18-56° C. This allows the eluted DNA to be concentrated in the device.

In the device above, the first chamber has a surface comprising a polymeric covering. This covering allows an interface with a vibrating device (sonicator or piezobuzzer) to aid cell lysis. The thin covering transfers energy without causing leakage from the vessel. During fabrication, the polymeric covering should be sonicated in isopropyl alcohol to remove combustion products of the laser-cutting process. After fabrication, the cards are preferably treated with ethylene oxide or gamma sterilization to remove competing pathogens. Off-card reagents preferably pass a 2 micron cellulose filter on entry to remove contaminants. The reagent ports on the card provide an interface to yellow and blue pipette tips. A needle-septum interface can be provided.

In one embodiment, the second chamber comprises at least one immobilized fluorescent compound having a fluorescence intensity dependent on the concentration of nucleic acids. In this embodiment the second chamber can include a window through which the fluorescence intensity of the fluorescent compound can be measured. In one embodiment, the fluorescent compound is immobilized in a region sufficiently proximate to the window so as to allow fluorescent measurement. The fluorescent compound may be a minor groove binder or an intercalating agent. In one embodiment, the fluorescent compound is a bis-benzimide compound (e.g., hexylamine modified bis-benzimide).

In one embodiment, the vessel is a component of a system that further includes a device for eliciting and measuring the fluorescent intensity of the fluorescent compound(s). Suitable devices include the fluorimeter noted above.

Figure 20B:
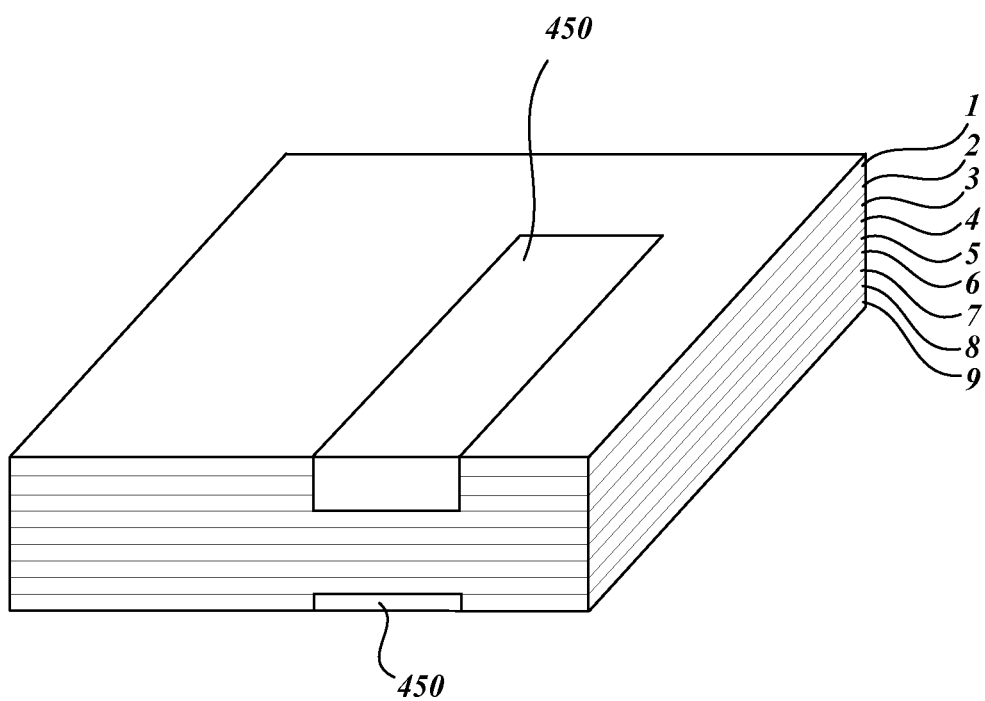
FIG. 20B is a schematic view of the assembled layers of a representative fluidic device of the invention having a glass surface on each side.

Representative devices of the invention were fabricated for DNA purification in a microfluidic card format. FIG. 1 illustrates a fabricated card. Glass slides are attached to the cards directly above and below the S-channel after the release layers are removed. The glass slides are aligned against the north edge and, once attached, sandwich the S-channel between them. The rectangular cutouts are 200 um wider than a standard glass slide. The combined layers are also illustrated schematically in FIGS. 1 and 20B, and the individual layers are illustrated in FIG. 20A. Primary features include two connector ports located on layer 9, a triangular chamber formed by layers 2-6, a serpentine channel (S-channel) formed by layers 4-8, and an alignment edge formed on the card bottom by layers 1-3 and on the card top by layer 9. The two ports (inlet 100 and outlet 600) requiring fittings are at the top of the card. Standard size glass slides are placed inside the cutout rectangles sandwiching the serpentine channel (S-channel). See FIGS. 1 and 20B, reference numeral 450.

FIG. 1 is a schematic illustration of a representative fluidic device of the invention, or DNA card. Referring to FIG. 1, card 10 includes fluid inlet 100 into a first chamber 200. First chamber 200 is connected to second chamber 400 by first channel 300. Second chamber 400 includes a serpentine S-channel and at least one glass surface 450. The card can be assembled with glass slides on both sides of the S-channel. Second chamber 400 is connected to fluid outlet 600 by second channel 500. In one embodiment, the second chamber is defined by layers 4-8 shown in FIG. 20A (S-channel) and two glass slides (floor and ceiling, see FIG. 20B).

FIG. 20A is an exploded view of a representative DNA card of the invention. The DNA card is fabricated with nine layers. Referring to FIG. 20A, layers 2-6 include first chamber 200.

Layers 4-8 include second chamber 400. Second chamber 400 has a serpentine S-channel, shown in layers 4-8. Layer 6 includes inlet 100 and first channel 300. Layer 8 includes second channel 500 and outlet 600. Glass surface 450 is positioned over the rectangular cut-out in layers 1-3, and a second glass surface 450 is positioned over the rectangular cut-out in layer 9. FIG. 20B is an assembled view of a representative DNA card of the invention.

There are several ways to input the sample and various wash buffers into the vessel, or card. In the initial design stage Peek tubing stubs were attached to the 9-layer laminated cards allowing manual input. Manual addition allowed the various buffers to be optimized for volume, incubation time, and flow rate. Alternatively, standard 1 ml polypropylene syringes or a programmable peristaltic pump can be used with tubing and Luer lock adaptors. The leak-proof property of the cards can be advantageously used to aliquot reagents from a reservoir tube.

In one embodiment the positions of the inlet and outlet are on the upper edge of the card. This will allow multiple cards to be lined up in a rack. The liquid lines will be connected to the tubing stubs using an O-ring seal to the pump head. A simple valve mechanism will switch buffer sources and will be coordinated with the programmable pump. Computer-controlled 12-channel peristaltic pumps (Ismatec) that can be programmed to start/stop/change flow rate or reverse direction of flow. A rack of twelve cards would be of about the same dimensions as the 12-channel pump. A separate Luer type port on the top side of the card can be added for addition of the sample. The (1 ml) syringe can remain in place during the entire lysis/DNA extraction/PCR process and be disposed of with the card after disconnecting from the instrument. Leaving the syringe in place ensures maintenance of a closed system.

A batch of cards were fabricated by Aline Inc. (Redondo Beach, Calif.) and underwent the following treatment at their facilities prior to shipping: (1) post-fabrication the parts were sonicated in 20% aqueous isopropyl alcohol for twenty minutes; (2) a vacuum was applied (25 mm Hg) and then isolated from the pump, after 16 hours, the parts did not have moisture inside, and the vacuum had decreased to 18 mmHg, the parts also developed more haze where the PSA degassed (typical behavior for this class of PSA); (3) tube stubs were then attached and plasma was run though the channel and chamber of each part, and the edges of the serpentine channel were also treated; and (4) the parts were then sealed into foiled barrier bags with a heat seal.

FIGS. 21A-21F are schematic illustrations of the transport of fluids through the fluidic device of the invention. Referring to FIG. 21A, card 10 is shown with sample 25 in first chamber 200. After lysis and incubation card 10 is rotated clockwise 90 degrees and sample 25 is transported through the first channel 300 into the S-channel of second chamber 400, as shown in FIG. 21B. DNA is captured on glass surface 450 of second chamber 400, and chaotropic salt solution is introduced into card 10 through outlet 600 (FIG. 21C). After washing card 10 is tipped again to transport waste reagents back to first chamber 200, where they are stored for disposal (FIGS. 21D-21F).

In a representative embodiment, the card is a ⅛ inch thick clear walled laminated device with 2 internal chambers and 2 connecting channels. The card is the size of a standard 96 well plate. The S-channel has glass walls formed by two glass microscope slides. Fluorescence can be measured in the S-channel using a standard plate reader. In use, 0.2 ml of sample is introduced through the inlet port (see FIG. 1, reference numeral 100) and lysed in the triangular lysis chamber. After lysis, the S-channel is filled by gravity (no micro valves needed). DNA is captured on the glass surfaces with high chaotropic salt. Wash buffers are pumped into outlet port inlet port (see FIG. 1, reference numeral 600) using a peristaltic pump or a syringe/pipetter. After washing, the DNA is eluted from the S-channel with low salt. FIG. 21 illustrates a gravity filling mode of the S-channel. After returning to the starting position, waste reagents are pumped back into the lysis chamber (now waste chamber) for safe disposal.

A more detailed description of a representative card and its features are as follows:
  connecting channel widths=1.0 mm;
  port diameter for all ports=1.0 mm;
  S-channel fits within the area of a standard glass slide, width=25.3 mm, length=75.5 mm;
  S-channel lines up with well positions of a standard 96 well microplate;
  glass slide separation distance (glass chamber thickness) =22 mils (558.8 um);
  S-channel volume (glass chamber volume)=509 ul;
  area covered by the S-channel is 910 mm$^2$, if both top and bottom glass surfaces are included, the total glass area exposed to liquids=1820 mm$^2$, which is approximately equivalent to the area of one surface of a single glass slide (1910 mm$^2$);
  lysis chamber was designed to be separate from the glass chamber;
  lysis chamber can be filled without allowing fluids to enter the S-channel;
  lysis chamber volume ≥815 ul;
  lysis chamber is 1.27 mm thick.
  exterior dimensions of the card without added fittings are approximately 126.8 by 84.8 mm by 2.24 mm (thickness), with added tube stubs thickness is approximately 10 mm.

The devices were assembled with glass microscope slides on both sides of the S-channel. The adhesive sealed well (no leaks with moderate pressure). The cards could be filled in a bubble free method by adding solutions via the outlet port. By filling from the bottom up, displaced air is removed via the inlet port. As designed, the S-channel has a volume of about 0.6 ml. In practice, the card was placed flat on the bench and peristaltic pump was connected to the outlet port and the pump was used to successfully move a 0.075 ml sample back and forth in the channel using a flow rate of 1 ml/min and manually reversing the pump direction.

FIGS. 22A and 22B are a schematic illustration of the device and method of the invention useful for nucleic acid amplification. Referring to FIG. 22A, second chamber 400 has a proximal end with first temperature zone 700 and a distal end with second temperature zone 800. First temperature zone 700 is at about 65° C. and second temperature zone 800 is at about 95° C. The first and second temperature zones are useful for thermal cycling for quantitative PCR in card 10. In one embodiment, a nucleic acid amplification reaction mixture containing a fluorescent probe and primers is added to isolated DNA in second chamber 400. The nucleic acid amplification reaction mixture and DNA combination 900 is transported back and forth between first temperature zone 700 and second temperature zone 800. Referring to FIG. 22B, an appropriate wavelength of excitation light is delivered with an LED and fluorescence intensity is detected with a photodiode housed in probe 1000. Fluorescence is detected through window 1100 in first temperature zone 700.

In another aspect, the invention provides a method for determining the microbial content of a blood product including:
  (a) introducing a sample of a blood product containing cells in a liquid medium into a first chamber of a vessel, the vessel comprising the first chamber and a second chamber, wherein the first chamber is in liquid communication with the second chamber, and wherein the second chamber has at least a portion of one surface effective for binding nucleic acids;

(b) contacting the cells in the liquid medium with a lysis buffer to provide nucleic acids in the liquid medium;

(c) transporting at least a portion of the liquid medium into the second chamber;

(d) extracting the nucleic acids from the liquid medium by binding the nucleic acids to the surface of the second chamber effective for binding nucleic acids to provide isolated nucleic acids;

(e) releasing the isolated nucleic acids from the surface of the second chamber effective for binding nucleic acids by contacting the isolated nucleic acids with an elution buffer to provide released nucleic acids;

(f) contacting the released nucleic acids with a nucleic acid amplification reaction mixture and a fluorescent compound having a fluorescence intensity dependent on the concentration of nucleic acids;

(g) measuring the fluorescence of the fluorescent compound to determine the quantity of released nucleic acids;

(h) treating the released nucleic acids and the nucleic acid amplification reaction mixture under conditions for amplifying the isolated nucleic acids by polymerase chain reaction to provide amplified nucleic acids; and (i) measuring the fluorescence of the fluorescent compound to determine the quantity of amplified nucleic acids.

In one embodiment the method includes repeating steps (h) and (i) a pre-determined number of times to determine the amount of amplified nucleic acids.

In one embodiment, the method further includes contacting the isolated nucleic acids in the second chamber with a wash buffer and removing the wash buffer from the second chamber. The wash buffer comprises a chaotropic salt solution.

In one embodiment, the fluorescent compound is immobilized in the second chamber.

In another embodiment, the lysis buffer comprises a chaotropic salt solution.

In yet another embodiment, the elution buffer comprises the fluorescent compound and the nucleic acid amplification reaction mixture.

In the above methods, the fluorescent compound is a bis-benzimide compound.

In one embodiment, the method further includes further incubating the sample for a pre-determined period of time prior to contacting the cells in the liquid medium with the lysis buffer. The pre-determined period of time can be 24 hours. For the specific application of the cards to bacterial contaminated platelet concentrate (PC), the sensitivity of the published PCR method is limited due to the small volume of platelet rich plasma (0.2 ml). In addition, the published method only used 10% of the initial extracted DNA from the PC. By combining culture amplification with PCR, a powerful bacterial detection technology can be created. Testing the freshly prepared PC after 24 hours of culture allows 1 bacteria/ml at time of sampling (day 1=day of PC prep). The combination of NAT and culture methods for sensitive detection of bacterial contaminated platelets has not previously been described. A suitable septum sealed aerobic culture bag (with media tablet) is sold by Pall (2 ml PC volume) and septum sealed aerobic and anaerobic culture bottles (4-8 ml PC) are sold by BioMeriuex. The DNA card could also serve as a suitable culture vessel if desired. This would allow all operations (cell culture, cell lysis, DNA extraction, DNA purification, DNA analysis, and NAT testing) to take place in a single, disposable "lab on a chip" design in accordance with the device and method of the invention.

With microbial contamination levels at 1 cfu/ml, there is a statistical probability of 50% that a single bacterium would not be present in a 0.3 ml sample. To circumvent this sampling issue, the device of the invention can be used in combination with a platelet storage bag, as described in WO 06/023725. A representative sample bag contains a culture broth pellet and is charged with 10 ml PRP. After 24 hours at 37° C., a small sample (0.2 ml volume) is enriched in microbial DNA and a 0.2 ml sample size will contain the genomic DNA target. Transfer of this sample to the device of the invention allows for PCR detection of the captured genomic DNA target. By coupling microbial culture with PCR, the invention provides a sensitive microbial contamination test having a reasonably short quarantine period for a day 1 test. The system ensures that no patient will receive a microbially-contaminated PC unit. The 24 hour culture period fits well in the blood bank environment since most PCs are transfused after 3 days of storage.

In another aspect the invention provides a method for quantifying and amplifying the amount of nucleic acids in a sample. The method includes:

(a) contacting nucleic acids from a sample with a nucleic acid amplification reaction mixture that comprises a first fluorescent compound having a first fluorescence emission maximum and a second fluorescent compound having a second fluorescence emission maximum, wherein the first and second fluorescence emission maxima are different, each having a fluorescence intensity dependent on the concentration of nucleic acids;

(b) measuring the fluorescence of the first fluorescent compound to determine the amount of nucleic acids;

(c) treating the nucleic acids and the nucleic acid amplification reaction mixture under conditions for amplifying the nucleic acids to provide amplified nucleic acids; and (d) measuring the fluorescence of the second fluorescent compound to determine the amount of amplified nucleic acids.

In one embodiment, the nucleic acid amplification reaction mixture further includes a third fluorescent compound having a third fluorescence emission maximum and a fluorescence intensity dependent on the concentration of amplified nucleic acids, wherein the third fluorescence emission maximum is different from the first and second fluorescence emission maxima.

In one embodiment, the second and third fluorescent compounds are oligonucleotide probes, each specific for a particular gene or gene product.

In another embodiment, the first fluorescent compound is a minor groove binder or an intercalating agent. The first fluorescent compound can be a bis-benzimide compound, such as a hexylamine modified bis-benzimide compound.

In another aspect, the invention provides a composition including a nucleic acid amplification reaction mixture and a fluorescent compound. The fluorescent compound has a fluorescence intensity dependent on the concentration of nucleic acids and has a fluorescent emission maximum less than about 500 nm. The emission wavelength less than about 500 nm assures that the blue emitting fluorescent compound can be quantitated in the presence of other green and red emitting probes having emission maxima greater than about 500 nm. The composition is useful in methods for quantitating nucleic acids in the methods described above.

The following examples are provided for the purpose of illustrating, not limiting the invention.

EXAMPLES

Example 1

Lysis and DNA Extraction Using Glass Slides 200 ul of a sample such as blood, plasma, buffy coat, platelet concentrates as well as any nucleic acid from the organism from which the sample is obtained in addition to any exogenous (bacterial, fungal, or parasitic) nucleic acids found in the sample is mixed with 200 ul of a lysis buffer (described below) and subsequently incubated with 20 ul proteinase K of a specific activity of at 5-7.5 AU Anson Units at 56-65C for 15 minutes.

The source of the purified Proteinase K is the yeast *Pichia pastoris* as it would be predicted to contain fewer contaminating bacterial DNA molecules which could be used to identify microbial contamination in the sample. A well known property of this enzyme is its activity across a broad range of pH (4-12.5) and an increase of its activity sevenfold in the presence of SDS at temperatures ranging between 56° C. and 65° C.

The lysis buffer is composed of 1-3M GuSCN at a pH of 5-6.0 with 0.5 to1.2% Triton X-100 or mixtures of other detergents (such as SDS, NP40, CTAB, CHAPS, Sarkosyl, and Tween 20). Following this incubation the lysate is heated further to 95° C. for 2-10 minutes and then cooled slightly to a temperature of <65° C. The lysate is then subjected to mechanical disruption of the biological materials using a sonicator probe, or a piezobuzzer device, or another similar device capable of introducing high frequency resonant vibrations to the sample through a lysis chamber wall of the DNA purification device (as described below) or directly by probe sonication at 350 MHz for 90 seconds (three 30 second bursts) directly in an Eppendorf tube. The entire lysate is subsequently loaded onto a surface composed of two standard microscope slides separated by a distance of at least 0.417 mm and incubated for about 20-30 minutes. Following about 20 minutes of adsorption at a temperature between 18 and 60° C. the glass slides are washed with 500 ul Buffer AW1 [pH ~5.5 57% Ethanol] containing GuSCN. Subsequently 500 ul of Buffer AW2 [pH 7.5 70% Ethanol] are added in order to rinse each set of slides two times in successive order. Following the two washes the slides are spun dry in an Allegra 6 (or similar) centrifuge at <2K for 10 minutes. Elution of the DNA is carried out next (200 ul) Buffer TE [pH 8.5] or distilled water by incubating at a temperature between (18-70° C.) for 5-20 minutes, and then centrifuging in an Allegra 6 centrifuge at <2K for 10 minutes.

Example 2

Basic Fluidic Protocol for the Use of a Representative Device of the Invention A description of the use of a representative device of the invention, a fluidics card, developed to facilitate the DNA extraction performance (sample is platelet concentrate (PC), a mixture of plasma with albumin, fibrinogen, a few leukocytes (1 M), and a high concentration of platelets (about $1\times10^8$)) in a closed system environment is as follows:
  a. Add 0.2 ml of PRP to the lysis chamber;
  b. Add 0.2 ml of lysis buffer (with proteinase K or other protease) and mix (2 minutes);
  c. Incubate at 65° C. (5 minutes);
  d. Incubate lysis chamber at 95° C., then cool to <65° C., creating a lower viscosity solution (2 minutes);
  e. (Option 1) Further disrupt the biological materials using a device capable of introducing high frequency resonant vibrations to the sample through a lysis chamber wall (2 minutes);
  f. Add 0.2 ml of ethanol and mix (1 minute), viscosity of solution is similar to water;
  g. Tip card to flow lysate into the glass-walled S-channel;
  h. Incubate 5-30 minutes at ambient temperature;
  i. Tip card back to start position;
  j. Pump in 0.6 ml of wash #1 buffer (incubate 1 minute);
  k. Pump in 0.6 ml of wash #2 buffer (incubate 1 minute);
  l. Purge wash #2 from glass walled S-channel with air stream (1 minute);
  m. Fill S-channel with 50-500 ul of elution buffer containing BB dye;
  n. (Option 2) Pump elution buffer back and forth in S-channel (5 minutes);
  o. Read the dye fluorescence (460 nm) to quantitate DNA present;
  p. Remove purified DNA solution from card and aliquot for PCR;
  q. (Option 3—elution buffer contains PCR reagents) Pump PCR reagents back and forth between 65° C. and 95° C. temp zones (5-30 minutes);
  r. Read blue fluorescence at each PCR cycle (real-time PCR);
  s. Analyzed data and quantitate microbial load (if any); and
  t. Report results The multiple processing steps point to the benefit of the lab-on-a-chip format. A programmable pump and valve system can be used to add the various reagents to the card, and the incubation steps are controlled by the position of the fluids in a thermally controlled instrument. Fluorescent reading of the DNA containing fluids in the card will be directly through the glass microscope slides themselves. Assuming 10 minutes are needed for the DNA binding (step h), purified DNA (PCR ready) can be isolated in 30 minutes. Some steps can also be shortened or eliminated depending on the sensitivity requirements for microbial detection. The quantitative PCR thermal cycling can be executed within 30 minutes or less. The trim S-channel allows rapid temperature equilibration and permit efficient primer extension.

The embodiments of the invention in which an exclusive property or privilege is claimed are defined as follows:

1. A method for quantifying and amplifying the amount of nucleic acids in a sample, comprising:
  (a) contacting nucleic acids from a sample with a nucleic acid amplification reaction mixture comprising a first fluorescent compound having a first fluorescence emission maximum, a second fluorescent compound having a second fluorescence emission maximum, and a third fluorescent compound having a third fluorescence emission maximum and a fluorescence intensity dependent on the concentration of amplified nucleic acids, wherein the first, second, and third fluorescence emission maxima are different, each having a fluorescence intensity dependent on the concentration of nucleic acids;
  (b) measuring the fluorescence of the first fluorescent compound to determine the amount of nucleic acids;
  (c) treating the nucleic acids and the nucleic acid amplification reaction mixture under conditions for amplifying the nucleic acids to provide amplified nucleic acids; and (d) measuring the fluorescence of the first fluorescent compound to determine the amount of amplified nucleic acids.

2. The method of claim 1, wherein the first fluorescent compound is a minor groove binder or an intercalating agent.

3. The method of claim 1 further comprising measuring the fluorescence of the second fluorescent compound to determine the presence of a gene or gene product.

4. The method of claim 1, wherein the second fluorescent compound is an oligonucleotide probe.

5. The method of claim 1 further comprising measuring the fluorescence of the third fluorescent compound to determine the presence of a gene or gene product.

6. The method of claim 1 wherein the third fluorescent compound is an oligonucleotide probe.

7. A method for quantifying and amplifying the amount of nucleic acids in a sample, comprising:
(a) contacting nucleic acids from a sample with a first fluorescent compound having a first fluorescence emission maximum and a fluorescence intensity dependent on the concentration of nucleic acids;
(b) measuring the fluorescence of the first fluorescent compound to determine the amount of nucleic acids;
(c) treating the nucleic acids with a nucleic acid amplification reaction mixture under conditions for amplifying the nucleic acids to provide amplified nucleic acids, wherein the nucleic acid amplification reaction mixture comprises a second fluorescent compound having a second fluorescence emission maximum and a fluorescence intensity dependent on the concentration of nucleic acids, and a third fluorescent compound having a third fluorescence emission maximum and a fluorescence intensity dependent on the concentration of nucleic acids, wherein the first, second, and third fluorescence emission maxima are different; and
(d) measuring the fluorescence of the second fluorescent compound to determine the presence of a gene or gene product.

8. The method of claim 7 further comprising measuring the fluorescence of the first fluorescent compound to determine the amount of amplified nucleic acids.

9. The method of claim 7, wherein the first fluorescent compound is a minor groove binder or an intercalating agent.

10. The method of claim 7, wherein the second fluorescent compound is an oligonucleotide probe.

11. The method of claim 7, wherein the third fluorescent compound is an oligonucleotide probe.

12. The method of claim 7 further comprising measuring the fluorescence of the third fluorescent compound to determine the presence of a gene or gene product.

* * * * *